(12) United States Patent
Pelati

(10) Patent No.: US 11,179,702 B2
(45) Date of Patent: Nov. 23, 2021

(54) PROCESS TO PREPARE INSOLUBLE POLYMER ABATEMENT ADDITIVES IN STYRENE PROCESS STREAMS BY CATALYTIC OXIDATION

(71) Applicant: Fina Technology, Inc., Houston, TX (US)

(72) Inventor: Joseph E. Pelati, Houston, TX (US)

(73) Assignee: FINA TECHNOLOGY, INC., Houston, TX (US)

( * ) Notice: Subject to any disclaimer, the term of this patent is extended or adjusted under 35 U.S.C. 154(b) by 77 days.

(21) Appl. No.: 16/687,820

(22) Filed: Nov. 19, 2019

(65) Prior Publication Data
US 2021/0146342 A1   May 20, 2021

(51) Int. Cl.
*B01J 23/75* (2006.01)
*B01J 23/28* (2006.01)
(Continued)

(52) U.S. Cl.
CPC ............ *B01J 23/75* (2013.01); *B01J 23/28* (2013.01); *B01J 23/34* (2013.01); *B01J 23/745* (2013.01); *B01J 35/1014* (2013.01); *B01J 35/1038* (2013.01); *B01J 35/1057* (2013.01); *B01J 37/0201* (2013.01); *B01J 37/0236* (2013.01); *C07C 45/28* (2013.01); *B01J 21/12* (2013.01); *B01J 2219/00002* (2013.01); *C07C 47/54* (2013.01); *C07C 49/78* (2013.01)

(58) Field of Classification Search
CPC ... B01J 21/12; B01J 23/28; B01J 23/34; B01J 23/745; B01J 23/75; B01J 35/1014; B01J 35/1038; B01J 35/1057; B01J 37/0201; B01J 37/0236; B01J 2219/00002; C07C 45/28; C07C 47/54; C07C 49/78
See application file for complete search history.

(56) References Cited

U.S. PATENT DOCUMENTS 3,709,979 A * 1/1973 Chu ................. C10G 11/04
423/700
5,206,201 A * 4/1993 Kishimoto ............ B01J 23/002
502/206

(Continued)

OTHER PUBLICATIONS

Saux, C. et al. (2011) Applied Catalysis A: General, 400(1-2), 117-121.*

(Continued)

*Primary Examiner* — Brian A McCaig
(74) *Attorney, Agent, or Firm* — Albert Shung

(57) ABSTRACT

An oxidation catalyst for the oxidation of styrene to benzaldehyde and acetophenone, the oxidation catalyst comprising: a porous support; and an active phase comprising an oxygen activation metal comprising cobalt (Co), manganese (Mn), iron (Fe), molybdenum (Mo), or a combination thereof. A method of forming the oxidation catalyst, a method of forming an oxidation product comprising benzaldehyde and acetophenone by contacting the oxidation catalyst with styrene and air in an oxidation reactor, and a system and method for reducing the fouling in a process for the production of styrene by introducing an additive stream comprising at least a portion of the oxidation product into a stream comprising styrene and byproduct divinyl benzene (DVB) are also disclosed.

14 Claims, 10 Drawing Sheets

(51) Int. Cl.
*B01J 23/34* (2006.01)
*B01J 23/745* (2006.01)
*B01J 35/10* (2006.01)
*B01J 37/02* (2006.01)
*C07C 45/28* (2006.01)
*B01J 21/12* (2006.01)
*C07C 47/54* (2006.01)
*C07C 49/78* (2006.01)

(56) References Cited

U.S. PATENT DOCUMENTS

| | | | |
|---|---|---|---|
| 6,680,013 B1 * | 1/2004 | Stein | B29C 67/202 264/44 |
| 7,541,310 B2 | 6/2009 | Espinoza et al. | |
| 2012/0122653 A1 * | 5/2012 | Maesen | B01J 23/8885 502/5 |
| 2016/0121305 A1 * | 5/2016 | Kartick | B01J 37/0201 252/373 |

OTHER PUBLICATIONS

Nie, L. et al. (2007) Catalysis Communications, 8, 488-492.*
Haber, J. et al. (1995). Pure and Applied Chemistry, 67(8/9), 1257-1306.*
PCT/US2020/061236 International Search Report and Written Opinion dated Apr. 6, 2021 (18 p.).
Liu, Jiangyong et al., "Highly Selective Oxidation of Styrene to Benzaldehyde over a Tailor-Made Cobalt Oxide Encapsulated Zeolite Catalyst," Journal of Colloid and Interface Science, vol. 517, Feb. 2, 2018, pp. 144-154 (11 p.).
Jean-Marie, Alan et al., "Cobalt Supported on Alumina and Silica-Doped Alumina: Catalyst Structure and Catalytic Performance in Fischer-Tropsch Synthesis," Comptes Rendus Chimie, Elsevier, Paris, FR, vol. 12, No. 6-7, Jun. 1, 2009, pp. 660-667 (8 p.).
Oliveira, Ana Paula Saraiva et al., "Styrene Oxidation to Valuable Compounds over Nanosized FeCo-Based Catalysts: Effect of the Third Metal Addition," Catalysts, vol. 7, No. 11, Oct. 30, 2017, p. 323 (27 p.).

* cited by examiner

PROCESS TO PREPARE INSOLUBLE POLYMER ABATEMENT ADDITIVES IN STYRENE PROCESS STREAMS BY CATALYTIC OXIDATION

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

This disclosure relates to the production of styrene monomer. More particularly, the disclosure relates to reducing the polystyrene fouling encountered in the production of styrene monomer, which fouling can result in production loss due to reduced rates. Still more particularly, the disclosure relates to reducing the amount of insoluble polystyrene polymer formed during styrene production, via the production of an oxidation product comprising benzaldehyde and acetophenone from a process stream comprising styrene, and introduction of at least part of the oxidation product into a process stream comprising styrene.

BACKGROUND

Styrene, a raw material for major polymer products such as polystyrene, acrylonitrile butadiene styrene, styrene butadiene rubber, and others, is consumed in great quantities annually, being one of the representative general-purpose monomer products. It is well-known that styrene can be prepared by dehydrogenating ethylbenzene (EB) in the presence of superheated water vapor, i.e. steam, on a dehydrogenation catalyst bed in a reactor. Styrene manufacturing plants generally utilize a reaction system comprising two or three adiabatic reactors connected in series, in conjunction with a number of furnaces and heat exchangers.

Conventional manufacturing of styrene, for example via EB dehydrogenation, produces a crude styrene stream that typically contains about 60% styrene. Purification by distillation encounters challenges due to the thermal self-initiation of polymerization by styrene that can occur at a significant rate above 80° C. Styrene boils at 145° C., so distillation is generally carried out at lower pressure and temperature with the addition of polymerization inhibitors (also called anti-polymerization agents or polymerization retarders). In order to control unwanted monomer degradation and/or unwanted formation of polystyrene polymer during styrene manufacture, a polymerization retarder is commonly added to the process. Typical products used for this purpose are dinitrophenols such as DNOC (di-nitro-ortho-cresol) or DNBP (di-nitro-sec-butyl-phenol) as well as quinone derivatives and true inhibitors, molecules that react with radicals faster than the propagation rate, such as substituted tetramethylpiperidene-1-oxyl species. Despite being effective in controlling styrene polymerization, some of these retarders can be highly toxic and/or rather costly. The true inhibitors are rapidly consumed and may not be effective in some areas.

The use of true inhibitors has stopped nearly all soluble polymer formation in the styrene distillation columns, however insoluble polymer deposits are found at turnarounds even after good, normal runs are made. During times of serious events or mechanical issues, insoluble polymer fouling can be severe. Insoluble polymer fouling can cause loss of availability, capacity and efficiency. Distributors, trays and structured packings of the distillation columns are susceptible to damage from this type of fouling; full shutdowns may be needed to remove the fouling and repair the damage. If the column packing is fouled, it has to be replaced. Costly extended outages and major repairs are possible due to acute insoluble polymer fouling. Thus, there are multiple circumstances in which insoluble polymer will cause losses.

The ubiquitous by-product, divinyl benzene (DVB), is a potent cross-linking agent that can lead to the production of insoluble DVB cross-linked polystyrene polymer (also referred to herein as insoluble polymer and/or DVB cross-linked polymer). Substantial amounts of insoluble polymer are often observed in styrene distillation systems even with the use of conventional distillation polymerization inhibitors. Insoluble polymer fouling in styrene production plants can cause issues such as flow restrictions, reduced heat exchange and loss of distillation column performance. The use of modern polymerization inhibitors/retarders, even with high dosages, has not eliminated the formation of insoluble polymer. DVB has a boiling point of 195° C. and may concentrate in hot, liquid form in areas where styrene and EB remain in the gas phase. Such areas could be locations where insoluble polymer could initiate. It is feasible that cross-linked polymer radical masses form in such locations. After formation, these insoluble polymer 'seeds' could migrate to other areas where they can settle and form large deposits of insoluble polymer over time. Deposits of insoluble polymer thus remain an issue for conventional styrene production.

Accordingly, there exists a need for improved methods of styrene production and/or purification whereby insoluble polymer formation is inhibited.

SUMMARY

Herein disclosed is an oxidation catalyst for the oxidation of styrene to benzaldehyde and acetophenone, the oxidation catalyst comprising: a porous support; and an active phase comprising an oxygen activation metal comprising cobalt (Co), manganese (Mn), iron (Fe), molybdenum (Mo), or a combination thereof.

Also disclosed herein is a method of producing an oxidation catalyst, the method comprising: forming an aqueous solution of an active metal precursor, wherein the active metal comprises cobalt (Co), manganese (Mn), iron (Fe), molybdenum (Mo), or a combination thereof, impregnating a support with the aqueous solution to form an impregnated support; and calcining to form the oxidation catalyst.

Further provided is a method of forming an oxidation product comprising benzaldehyde and acetophenone, the method comprising: contacting the oxidation catalyst of this disclosure with styrene and air in an oxidation reactor at a pressure of greater than or equal to atmospheric pressure and less than a pressure of 1, 3, or 5 atm.

Also disclosed herein is a method of reducing the fouling in a process for the production of styrene, the method comprising: producing, via oxidation of a crude styrene stream, a tar stream comprising styrene, or a combination thereof, an oxidation product comprising benzaldehyde, acetophenone, or a combination thereof, wherein the oxidation is effected with the oxidation catalyst of this disclosure; and introducing an additive stream comprising at least a portion of the oxidation product into a stream comprising styrene and byproduct divinyl benzene (DVB), whereby divinyl benzene (DVB) crosslinking is inhibited.

Also disclosed is a system for the production of styrene via dehydrogenation of ethylbenzene (EB), the system comprising: one or more dehydrogenation reactors operable to contact EB and steam with a dehydrogenation catalyst under dehydrogenation conditions to yield a crude styrene effluent comprising styrene and byproduct divinyl benzene (DVB); a heat exchange apparatus configured to reduce the temperature of the crude styrene effluent to provide a cooled crude styrene effluent; a separations apparatus configured to separate an offgas and/or a condensate from the cooled crude styrene effluent and thus provide a dehydrogenation mixture, a distillation section operable to separate the dehydrogenation mixture into one or more streams comprising benzene, toluene, ethylbenzene, or a combination thereof, a tar stream comprising polymer, additives, species having a higher boiling point than that of styrene, and styrene, and a stream comprising styrene; an oxidation unit configured to produce, via oxidation of a portion of the tar stream, an oxidation product stream comprising oxidation products including benzaldehyde, acetophenone, or a combination thereof, wherein the oxidation unit comprises the oxidation catalyst of this disclosure; and one or more recycle lines whereby at least a portion of the oxidation product stream can be combined with the crude styrene effluent, the cooled crude styrene effluent, the dehydrogenation mixture, a feed, recycle, or reflux to a distillation column of the distillation section, or a combination thereof.

BRIEF DESCRIPTION OF THE DRAWINGS

The detailed description will reference the drawings briefly described below, wherein like reference numerals represent like parts.

DETAILED DESCRIPTION

Overview

Figure 1:
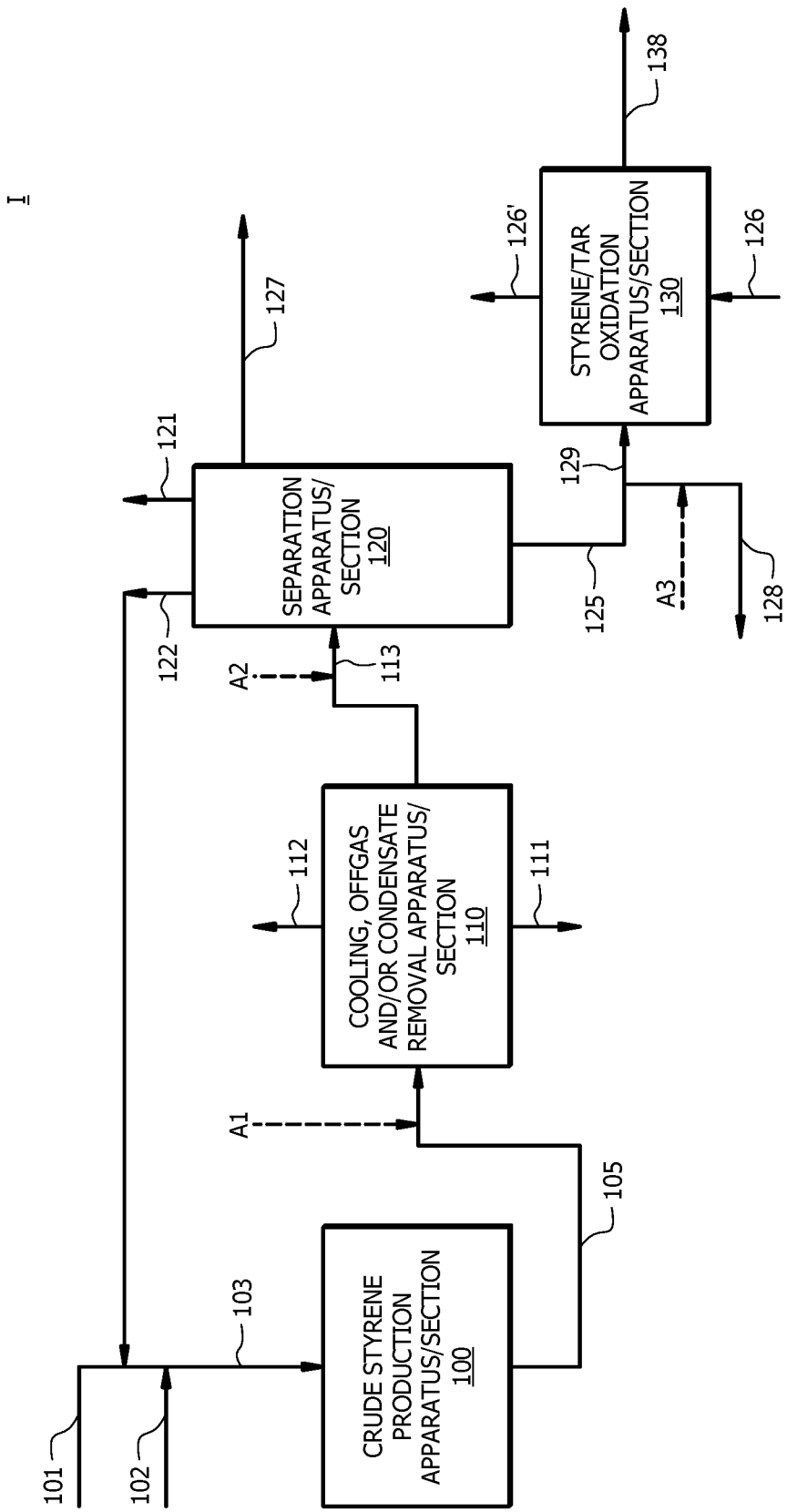
FIG. 1 is a process flow diagram of a styrene production system I according to an embodiment of this disclosure.

It should be understood at the outset that although illustrative implementations of one or more aspects are illustrated below, the disclosed additives, compositions, systems, and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. While values for dimensions of various elements are disclosed, the drawings may not be to scale.

As noted above, styrene produced by the high temperature dehydrogenation of ethylbenzene (EB) contains low-level by-products, such as divinyl benzene (DVB), which can lead to insoluble polymer fouling. Deposits of insoluble, DVB-crosslinked polymer can be a serious issue for styrene plants. The issue is exacerbated by the fact that the run lengths for such plants may last three years or longer. Herein disclosed are insoluble polymer abatement additives or IPAAs (also referred to herein simply as additives) that can reduce or inhibit such insoluble polymer formation, along with the concomitant fouling (e.g., DVB fouling effects), compositions comprising such additives, and methods of reducing the fouling encountered during production and/or purification of styrene. Such IPAAs have boiling points near that of DVB and having sufficient chemical activity to inhibit DVB from forming insoluble polymer (e.g., to inhibit the formation of DVB cross-linked polystyrene).

Standard polymerization inhibitors appear to suppress DVB reactions when present, however, such polymerization inhibitors are typically expensive, toxic, and high-boiling (e.g., boiling above 200° C. at atmospheric pressure). It has been discovered that a composition as described herein comprising at least one IPAA (also referred to herein as a 'chemical component' or "chemical compound") having a boiling point near that of DVB can be effective to address possible sites of condensation and reaction of DVB. By having a boiling point near that of DVB (and lower than that of conventional polymerization inhibitors), the IPAA(s) can remain with (or 'follow') the DVB during the styrene purification process. Without wishing to be limited by theory, such sites of DVB condensation may be a source of 'seed' polymer that leads to insoluble polymer deposits, and IPAAs as described herein having appropriate properties for interacting with DVB and following the DVB (i.e., remaining with the DVB throughout most of the styrene purification/post-production processing) may reduce such seeding, along with the resulting insoluble polymer fouling.

Unless otherwise noted, boiling points listed herein are standard boiling points at 1 atmosphere pressure. In embodiments, the at least one chemical compound or IPAA boiling near that of DVB has a boiling point that is within 5, 10, 20, 30, 40, 50, or 60° C. of the boiling point of DVB, which is 195° C., and sufficiently higher than the boiling point of styrene (145° C.) to allow effective separation from styrene. In embodiments, a temperature sufficiently higher than the boiling point of styrene is at least 170° C. That is, in embodiments, the at least one chemical component has a boiling point in the range of from 190° C. to 200° C., from 185° C. to 205° C., from 175° C. to 215° C., from 170° C. to 225° C., from 170° C. to 235° C., from 170° C. to 245° C., or from 170° C. to 255° C. In embodiments, the IPAA has a boiling point less than or equal to that of DVB, i.e., less than or equal to 195° C. In embodiments, the IPAA has a boiling point greater than or equal to that of styrene, i.e., greater than or equal to 145° C. and desirably higher than 170° C. to allow effective separation by distillation. In embodiments, the IPAA has a boiling point of less than or equal to about 260° C., 250° C., 240° C., 230° C., 220° C., 210° C., 200° C., or 195° C., has a boiling point of greater than or equal to about 170° C., 180° C., 190° C., 200° C., 210° C., 220° C., or 230° C., or some range therein delineated.

The IPAA also comprises one or more functional groups such that it is active to inhibit DVB crosslinking. As used herein, an IPAA is 'active to inhibit DVB crosslinking' if purification of a crude styrene comprising styrene and DVB in the presence of the IPAA produces less insoluble polymer (which may, in instances, be indicated by a smaller decrease in molecular DVB) than the same process absent the IPAA. Such analysis may be performed, for example, via the technique described in Example 1 herein below. A method according to this disclosure may provide for reduced fouling during the production/purification of styrene. Such a reduction in fouling may comprise a reduction in the formation of insoluble polystyrene, soluble polystyrene, or both, relative to the same process absent the IPAA.

Several different chemical moieties (e.g., labile C—H and C—C bonds, oxygen and nitrogen functional groups) have been found to have the ability to inhibit the undesirable reaction of DVB, and retard DVB crosslinking. In embodiments, the IPAA comprises appreciably active oxygen, such as provided by, without limitation, alcohols, aldehydes, ketones, esters and carbonates. In embodiments, the IPAA comprises reactive hydrogen functional groups, such as provided by, without limitation, strained cyclics and carbonyls with beta hydrogens. In embodiments, the one or more functional groups are selected from amines, alcohols, amino-alcohols, labile C—C, esters, carbamates, aldehydes, ketones, acids, acetates, benzoates, labile hydrogen, glycols, or combinations thereof. In embodiments, the IPAA is selected from amines, glycols, benzoates, carbamates, or combinations thereof. Without wishing to be limited by theory, a key chemical property, in addition to the aforementioned boiling point, may be a chemical lability sufficient to interfere with radical chain polymerization. Moreover, some species may be able to chemically react with DVB at typical styrene distillation conditions.

Suitable IPAAs include, without limitation, ethyl lactate, tetralin, acetophenone, propylene glycol, di-propylene glycol, dipropylene glycol methyl ether, trans-stilbene, N,N-diethyl-1,4,-phenylenediamine, phenylethanol (e.g., 1-phenylethanol), benzaldehyde, benzaldehyde dimethyl acetal, diphenyl carbonate, methyl carbamate, ethyl carbamate, methyl benzoate, ethyl benzoate, ethylaceto acetate, diethylaminoethanol, biphenyl, diethanolamine, 3-amino-1-propanol, terpineol, or a combination thereof.

Without wishing to be limited by theory, the IPAA may be active to inhibit DVB crosslinking by consuming DVB (e.g., causing incorporation thereof into soluble polymer or otherwise reacting with DVB), preventing its incorporation into radical polymerization, or some other mechanism. For example, as seen in Example 1 herein below, benzaldehyde may react with DVB and thus effectively remove it from the process stream, and alkyl benzoates appear to suppress DVB reactivity by another mechanism. Addition reactions including, but not limited to, the Diels-Alder Reaction may occur to remove DVB from the process.

A herein-disclosed insoluble polymer abatement composition (IPAC) may comprise more than one IPAA active to inhibit DVB crosslinking and having a boiling point near that of DVB. For example, in embodiments, the additive comprises one such chemical component having a boiling point below that of DVB (i.e., less than 195° C.), and another such chemical component having a boiling point above that of DVB (i.e., greater than 195° C.). Such an additive mixture may be operable to span vapor pressure regions and thus provide broad coverage for retarding DVB reactivity. Such mixtures containing species having boiling points that are higher and lower than DVB may, for example, provide broad coverage in the condensation areas and distillation columns.

The IPAA may further enhance overall performance when used with a conventional polymerization inhibitor. In embodiments, an IPAC of this disclosure thus further comprises a conventional polymerization inhibitor. Generally, such conventional polymerization inhibitors have much higher boiling points than the chemical components described herein. For example, conventional polymerization inhibitors may have boiling points of greater than 195° C., 200° C., 205° C., 215° C., 225° C., 235° C., 245° C., 250° C., or 300° C. Such polymerization inhibitors include, without limitation, those comprising dinitrophenols (e.g., DNOC (di-nitro-ortho-cresol) or DNBP (di-nitro-sec-butylphenol)), quinone derivatives, TMPO compounds (e.g., 4-hydroxy-2,2,6,6-tetramethylpiperidine 1-oxyl, (2,2,6,6-tetramethylpiperidin-1-yl)oxyl or (2,2,6,6-tetramethylpiperidin-1-yl)oxidanyl), oximes (e.g., alternative retarder), and the like, available from multiple commercial vendors.

According to embodiments, a method of reducing the fouling in a process for the production of styrene according to this disclosure comprises introducing an IPAA or IPAC as described hereinabove into a stream comprising styrene and byproduct divinyl benzene (DVB). In embodiments, the stream comprising styrene and DVB is a crude styrene formed in a reactor configured to produce styrene. The crude styrene may be a product of ethylbenzene (EB) dehydrogenation, whereby EB is dehydrogenated in the presence of overheated water vapor, i.e. steam, as per Equation (1):

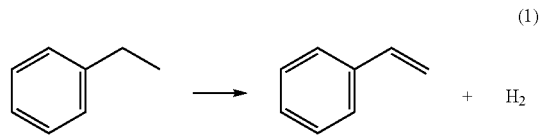

(1)

Systems and methods for producing such a crude styrene product are known in the art, and, in embodiments, the crude styrene is produced via any such known system and method. For example, a multi-stage EB dehydrogenation system and method are described in U.S. patent application Ser. No. 15/838,569, filed Dec. 12, 2017, which is hereby incorporated herein by reference in its entirety for purposes not contrary to this disclosure. Systems and methods for producing such a crude styrene are described in more detail herein below.

In embodiments, the IPAA or IPAC is introduced at a concentration in a range of from about 0.001 to about 0.1, from about 0.01 to about 0.1, from about 0.001 to about 0.2, or equal to about 0.001, 0.01, or 0.1 weight percent of the stream comprising styrene and DVB. The stream comprising styrene into which the IPAA or IPAC is introduced may be a crude styrene reactor effluent of an EB dehydrogenation reactor, in embodiments. In embodiments, the stream comprising styrene into which the IPAA or IPAC is introduced is a feed, recycle, or reflux stream to a distillation column (or other purification unit) of a styrene purification/recovery section downstream of a reactor (e.g., an EB dehydrogenation reactor) in which the crude styrene was produced. As discussed in more detail with reference to FIG. 2 herein below, the distillation column may comprise a distillation column configured for the separation of a tops product comprising EB from a bottoms product comprising styrene (which distillation column may also be referred to herein as an "EB recycle" or "EB separation" column), a distillation column configured for the separation of a tops product comprising benzene and toluene from a bottoms product comprising EB and styrene, or a distillation column configured for the separation of a tops product comprising styrene from a bottoms product comprising tar (which distillation column may also be referred to herein as a "styrene finishing column"). Such tar comprises some styrene, heavy byproducts, polymer, and/or polymerization inhibitors/retarders, and may also be referred to herein as "styrene tar" or "styrene/tar".

Also disclosed herein is a composition comprising such a crude styrene stream comprising styrene and by-product DVB, and an IPAA or IPAC as described herein above. As utilized herein, a "crude styrene stream" is a stream comprising styrene coming from a styrene process (e.g., an existing styrene process).

System for the Production/Purification of Styrene

A method for the production of styrene utilizing the herein-disclosed additives will now be described with reference to FIG. 1. FIG. 1 is a process flow diagram of a styrene production system I according to an embodiment of this disclosure. Styrene production system I comprises crude styrene production apparatus 100, cooling, offgas and condensate removal apparatus 110, separation or 'distillation' apparatus 120, and oxidation apparatus 130 as disclosed in this patent. Crude styrene production apparatus 100 is any apparatus operable to produce a crude styrene comprising styrene and DVB from reactants. The reactants may be introduced via one or more reactant feed lines. For example, in the embodiment of FIG. 1, first reactant line 101 and second reactant line 102 are combined to create reactant feed inlet line 103, which is fluidly connected with crude styrene production apparatus 100. The reactant feed may provide an approximately equal mass flow rate of EB and steam, in embodiments. Alternatively, first reactant line 101 and second reactant line 102 can both introduce reactant directly into crude styrene production apparatus 100. Crude styrene is removed from crude styrene production apparatus 100 via crude styrene effluent line 105. As discussed further herein below with reference to FIG. 2, in embodiments, the crude styrene is produced via dehydrogenation of EB. Systems and methods for the production of crude styrene via EB dehydrogenation are known in the art, and may be utilized, in embodiments, to provide the crude styrene. For example, a multi-stage EB dehydrogenation as described in U.S. Patent App. No. 62/436,653 may be employed, in embodiments.

Cooling, offgas and/or condensate removal apparatus 110 is operable to cool by heat exchange, the crude styrene effluent of crude styrene production apparatus 100, which is introduced thereto via crude styrene effluent line 105, and may be referred to herein as simply 'cooling apparatus' or 'condensation zone' 110. Cooling offgas and condensate removal apparatus 110 may also serve to separate an offgas and/or a condensate from the crude styrene, thus providing a crude styrene which has been degassed and from which condensate (e.g., water) has been removed (e.g., dewatered). Offgas line 112 may fluidly connect with cooling apparatus 110, whereby offgas can be removed therefrom, and condensate line 111 may fluidly connect with cooling apparatus 110, whereby condensate can be removed therefrom. In embodiments, offgas line 112 is associated with separations apparatus 120. Separations feed line 113 may fluidly connect cooling apparatus 110 with separation apparatus 120, whereby cooled crude styrene mixture (which may also be degassed and/or dewatered) can be introduced into separation apparatus 120.

Separation apparatus 120 is any apparatus operable to remove one or more byproducts, unreacted reactants, and heavy residue (e.g., tar) from the cooled styrene mixture, thus providing a purified styrene monomer stream. For example, separation apparatus 120 may be configured to separate an unreacted reactant stream (e.g., EB) which may be removed from separation apparatus 120 via unreacted reactant outlet line 122 for recycling back to crude styrene production apparatus 100, one or more byproduct streams which may be removed from separation apparatus 120 via one or more byproduct outlet lines 121, and tar containing some styrene, which may be removed via styrene/tar outlet line 125 from a purified styrene monomer (SM) stream, which may be removed from separation apparatus 120 via styrene monomer (SM) outlet line 127. In embodiments, the purified styrene monomer comprises less than 150, 100, or 75 PPM EB. Unreacted reactant outlet line 122 may fluidly connect separations apparatus 120 with crude styrene production apparatus 100, for example via line 101 and/or 103, whereby unreacted reactant may be recycled to produce additional crude styrene.

When crude styrene production apparatus 100 comprises one or more EB dehydrogenation reactors, the unreacted reactant may comprise EB, which may be recycled to crude styrene production apparatus 100, for example, via unreacted reactant outlet line 122, and the byproducts may comprise benzene and/or toluene, which may be removed from separation apparatus 120 via one or more byproduct outlet lines 121.

In embodiments, tar recycle and/or further processing are utilized, whereby at least a portion of the tar in styrene/tar outlet line 125 is recycled via one or more tar recycle and/or further processing lines 128 (228/328). In embodiments, a system of this disclosure comprises styrene tar recycle streams, whereby active, unused polymerization retarder can be returned to the feed to the separations section 120 (e.g., introduced into separations feed line 113). In some such embodiments, one or more tar recycle and/or further processing lines 128 (228 in the embodiment of FIG. 2) may be configured to recycle tar/heavy residue back to separations feed line 113 (213/313) or into any individual column within separation or distillation apparatus 120 (220/320).

As described further hereinbelow, all or, more likely, a portion of the styrene/tar stream in styrene/tar outlet line 125 may be used to feed a tar oxidation unit operation, via tar oxidation feed line 129, wherein components in the tar stream (e.g., styrene, and etc.) can be oxidized to hydrocarbon oxygenate IPAAs that can be recycled back to the separation section 120 to provide insoluble polymer abatement. For instance, without limitation, styrene in the tar oxidation feed line 129 can be oxidized to benzaldehyde, acetophenone and/or phenylethanol. These species can be effective for reducing insoluble polymer fouling. Other species in the tar in addition to styrene can also form such oxygenates and provide the same or similar effect. Thus, in embodiments, tar outlet line 125 is fluidly connected with oxidation unit or apparatus 130 via tar oxidation feed line 129.

Oxidation unit or apparatus 130 is any oxidation apparatus operable to oxidize at least a portion of the styrene/tar introduced thereto via styrene/tar outlet line 125 and tar oxidation feed line 129 to produce a liquid effluent 138 comprising at least one chemical component described hereinabove for use in the herein-disclosed additive. Air can be introduced into oxidation section 130 via air inlet line 126 and excess air removed therefrom via excess air removal line 126'. As described further with reference to the embodiment of FIG. 4, the liquid effluent 138 can be utilized as is and recycled back to the separating section 120 or one or more chemical components (e.g., IPAAs) as per this disclosure separated therefrom prior to use of the one or more separated IPAAs for insoluble polymer abatement within the styrene production system. For example, the tar may comprise some latent styrene monomer and/or other monomer/compounds, which may be converted (i.e., oxidized) to form a desirable oxygenated chemical component of an additive as described herein, such as, without limitation, acetophenone, phenylethanol and/or benzaldehyde. In embodiments, from about 0.01 to about 0.1, from about 0.1 to about 1 or from about 1 to about 3 wt % benzaldehyde, from about 0.01 to about 0.1, from about 0.1 to about 1, or from about 1 to about 3 wt % acetophenone and/or from about 0.001 to about 0.01, from about 0.01 to about 0.1, or from about 0.1 to about 0.3 wt % ppm of phenylethanol can be produced from the styrene tar stream. In an exemplary embodiment, lab batch reactors at 120° C. have shown the production of 1.4% benzaldehyde, 0.9% acetophenone and 50 ppm of phenylethanol using plant stream samples. It is noted that the oxidation unit operation can be used on the styrene tar and/or another stream from separation section 120 (220 in FIGS. 2 and 320 in FIG. 3 described hereinbelow) provided the stream comprises oxidizable species.

All or a portion of the liquid effluent stream 138 or an additive component stream comprising one or more additives separated therefrom (e.g., as described further with reference to FIGS. 2 and 3 hereinbelow) may be reintroduced elsewhere in the styrene production system for insoluble polymer abatement. The portion of the liquid effluent stream 138 or the additive component stream may be recycled back to the feed stream to separations (e.g., separations feed line 113) and/or another point within the separations section within separations apparatus 120. For example, as described further herein below, the portion of the liquid effluent stream 138 or the additive component stream may be combined with other additive components and/or introduced into the crude styrene effluent in crude styrene effluent line 105, into the cooled (and/or degassed and/or dewatered) crude styrene effluent in separations feed line 113, a feed, recycle, and/or reflux to a distillation column of the separation apparatus 120, or a combination thereof. An oxidation residue resulting from separation of the additive stream from the oxidation effluent stream may be recycled within the styrene production system, in embodiments. Although not indicated in the Figures, in embodiments, a portion of the styrene monomer, for example in purified styrene monomer outlet line 127 (227 in the embodiment of FIGS. 2 and 327 in the embodiment of FIG. 3, described hereinbelow) or elsewhere can be introduced into an oxidation unit (with or without the EB tar), to produce the oxygenated chemical component(s) IPAA(s) for use reducing insoluble polymer formation.

As discussed hereinabove, styrene, which has a boiling point of 145° C., thermally self-initiates polymerization in the liquid state (styrene polymerization does not occur in the gas phase), and the polymerization rate can be significant at temperatures above 80° C. The boiling point of DVB is 50° C. higher than the boiling point of styrene and can also thermally self-initiate polymerization, and thus there may be areas in a styrene production plant where DVB can accumulate in high concentrations by condensation. As noted above, insoluble polymer formation in styrene production plants is a persistent problem because DVB, a trace byproduct, is a potent crosslinking agent that produces insoluble polymer deposits in, for example, distillation columns, tanks and piping. Such residues continue to be found even with the use of modern inhibitors that nearly eliminate polymer formation in distillation columns. One explanation is that DVB has sufficient vapor pressure at process conditions that allows it to concentrate in specific uninhibited areas to trigger insoluble polymer formation, such that this type of fouling can be problematic even after the use of true inhibitors that have reduced the amount of soluble polymer formation to very low levels. Such areas could be locations where insoluble polymer formation initiates.

Two main areas of potential concern have been discovered, and it is within these areas that introduction (and/or the presence) of an IPAA or IPAC according to this disclosure may serve particularly useful, as the IPAA(s) have similar boiling points/vapor pressures to DVB and suitable chemical activity to inhibit such insoluble polymer formation. A first area is the point where gas phase crude styrene from styrene production reactors is first condensed to liquid. In this area, the higher boiling DVB could liquefy before styrene does, thus providing a location exposed to hot, liquid DVB. A second potential initiation area comprises the distillation columns of downstream separations/purification apparatus (e.g., within an EB recycle column(s), a styrene finishing column(s), within column reflux and/or tar recycle streams) where DVB vapor could condense without the presence of inhibitor/retarder. Once produced, such insoluble polymer could attach and grow with time, with the attachment occurring at the point of initiation and/or somewhere downstream therefrom. DVB could collect up-column from the injection point due to some fractional vapor pressure. The condensation of significant amounts of liquid DVB above the feed point in distillation columns can be increased in areas due to unusual flow anomalies. Current inhibitor options in use are much higher boiling species and may not accumulate where DVB does. The vapor-liquid equilibrium inside distillation columns containing styrene and DVB would explain how a finite amount of DVB is able to migrate up the column above the feed point. Conventional inhibitors and retarders have a much higher boiling point than DVB and do not follow DVB via vapor migration. In lab experiments, DVB has been observed to be transported up distillation columns via vapor transport. Thus, the location of DVB initiation may not be the same as attachment and growth. Insoluble polymer can absorb and hold styrene to facilitate its growth.

The process areas in FIG. 3, which is described further hereinbelow, that are highlighted with hatching are areas of concern for insoluble polymer formation. The condensation zone 310 is the point where large heat exchangers condense the reactor effluent into the liquid state. DVB condenses before styrene and can conceivably form insoluble seed polymer that could be swept downstream for deposition and growth. The EB recycle column D2 and the styrene finishing column(s) including D3 could have small particles of insoluble polymer form above the feed point from DVB vapors or at points throughout the column. Also any point where flow and distribution are impaired could create stagnant areas for DVB to collect and initiate insoluble polymer formation. The bottoms of these columns often contain large deposits of insoluble polymer at each turnaround. The insoluble polymer in the bottoms can grow regardless if it formed there or migrated there after forming elsewhere. As described herein, a solution to the initiation areas described above is the addition of IPAA species as described herein that have boiling points near that of DVB and also have some chemical activity for inhibiting polymer formation. The similar boiling point allows potential insoluble polymer abatement additives, IPAA, to track DVB and condense or collect simultaneously.

Accordingly, in embodiments, a method of reducing the fouling in a process for the production of styrene according to this disclosure comprises introducing an IPAA or IPAC, as described hereinabove, into one or more streams comprising styrene and byproduct divinyl benzene (DVB) within such a first area (via one or more additive inlet lines A1), within such a second area (via one or more additive inlet lines A2), and/or into another area (via one or more additive inlet lines A3).

For example, as indicated in FIG. 1, an IPAA or IPAC according to this disclosure may be introduced into crude styrene effluent line 105 via additive inlet line A1, prior to cooling of the crude styrene effluent in cooling apparatus 110, such that the additive is present within the first area noted above where gas phase crude styrene from styrene production reactors of crude styrene production apparatus 100 is first condensed to liquid. Alternatively or additionally, an IPAA or IPAC according to this disclosure may be introduced just prior to or during the purification of the cooled crude styrene, as indicated by additive inlet line A2 of FIG. 1. In this manner, the additive will be present in the second noted area of concern—in the distillation columns of downstream separations/purification apparatus 120 where DVB vapor could condense without the presence of inhibitor/retarder.

Alternatively or additionally, an IPAA or IPAC according to this disclosure may be introduced elsewhere, such as, without limitation, into a tar recycle stream, as indicated by additive inlet line A3 of FIG. 1. In such embodiments, one or more additive inlet lines A3 may be configured to introduce an additive according to this disclosure into one or more tar recycle lines 128 configured to recycle tar/heavy residue from tar outlet line 125 (and/or oxidation residue outlet line 136 discussed below) back to separations feed line 113 and/or to any individual column in the separation section.

As the first area (i.e., area at which gaseous crude styrene is first condensed to liquid within cooling apparatus 110) is generally at higher temperatures than the distillation columns of separations apparatus 120, an IPAA or IPAC introduced into the first area via an additive inlet line A1 may be disparate from an IPAA or IPAC introduced into the second area via an additive inlet line A2 and/or an IPAA or IPAC introduced into another area via an additive inlet line A3, in embodiments.

Production of Crude Styrene in Crude Styrene Production Apparatus

In embodiments, the crude styrene comprising styrene and DVB is produced in crude styrene production apparatus 100 via EB dehydrogenation. Such EB dehydrogenation may be performed conventionally as known in the art, with steam dilution, reduced pressure operation, and adiabatic reactors. For endothermic reactions, reheaters are located between the adiabatic reactors. The dehydrogenation reaction may be favored at low pressure, so the reactors are typically operated at reduced pressure (i.e., vacuum conditions) by installing a compressor(s) (e.g., a vacuum compressor(s)) on the effluent line. Modern plant designs may consist of two reactors in series for styrene production. Conventional three-bed reactor systems are arranged in series, and are common retrofit options for increasing plant capacity.

In embodiments, as described in U.S. Patent App. No. 62/436,653, a first two EB dehydrogenation reactors of a multi-stage dehydrogenation application may be operated in parallel, and the combined product streams thereof are fed to a common third reactor, thus enabling a lowering of the overall reactor pressure, a decrease in energy needs, and/or an increase in product selectivity, while maintaining desirable conversion.

In embodiments, the crude styrene is produced via conventional styrene manufacturing utilizing a reaction system comprising two or three adiabatic reactors connected in series, in conjunction with a number of furnaces and heat exchangers. The styrene can be prepared by dehydrogenating EB in the presence of overheated water vapor, i.e. steam, on a dehydrogenation catalyst bed in a reactor. In the process, EB is mixed in the gas phase with five to twelve times its volume in high temperature steam, and passed over a solid bed of catalyst. Most ethylbenzene dehydrogenation catalysts are based on ferric oxide, promoted by several percent potassium oxide or potassium carbonate.

In the dehydrogenation process, a high conversion rate of ethylbenzene and a high selectivity to styrene, which inhibits the generation of side products such as benzene and toluene, are desirable. Process parameters affecting dehydrogenation performance include the catalyst, reaction temperature, reaction pressure, space velocity, the mixing ratio of steam to hydrocarbon (e.g., ethylbenzene), and etc.

Since the dehydrogenation reaction of ethylbenzene is an endothermic reaction, a higher reaction temperature is advantageous to the reaction. However, when the reaction temperature is excessively high, the selectivity to styrene decreases, and a side-reaction, which generates benzene, toluene, or other byproducts, becomes dominant. Due to the rather great amount of reaction heat, the outlet temperature of a reactor is significantly lower than the inlet temperature of the reactor. To compensate for the temperature drop, conventional dehydrogenation processes employ multiple reactors, and an interstage energy addition is provided between the reactors.

In many reactions, water acts as a catalytic poison, however it is well known that water plays important roles in the dehydrogenation of ethylbenzene. Steam reacts with potassium and iron, generates active sites, supplies latent heat for powering the endothermic reaction, and removes deposited carbon (i.e., coke) that tends to form on the iron oxide catalyst through the water gas shift reaction. The potassium promoter of the catalyst enhances this decoking reaction. The steam also dilutes the reactant and products, shifting the position of chemical equilibrium towards products. Since substantial energy is needed to maintain steam at temperatures above 600° C., processes using the minimum amount of energy are preferred. When an excessive amount of steam is used at high temperature, an important active component of a dehydrogenation catalyst, i.e. potassium, is dissolved and eluted via a reactor outlet. This has been indicated as a main reason for deactivation of the catalyst.

Since the number of resulting product molecules is more than that of reactants, the conversion levels in the dehydrogenation of ethylbenzene decrease as the pressure increases. That is, lower pressure (or ethylbenzene partial pressure) favors the production of styrene by driving the equilibrium to products. It may thus be desirable to operate the EB dehydrogenation under as low a pressure as possible, without imparting too great a capacity load on the compressor(s). When the pressure is reduced, stability is increased due to a decrease in catalyst coking, and selectivity to styrene is also improved due to a relatively decreased extent of side-reactions, which produce byproducts consisting primarily of benzene and toluene. Consequently, pressure reduction is also considered very advantageous in the process, improving both conversion and selectivity. The dehydrogenation reactors can be operated under vacuum to enhance the conversion and selectivity. Typical overall conversions are about 60-63% for two reactors operated in series and 63-70% for three reactors operated in series. Selectivity to styrene is typically 92-97% molar.

Because styrene and ethylbenzene have similar boiling points, their separation requires large distillation towers and high return/reflux ratios. Thus, a desirable conversion may be maintained within the dehydrogenation reactors, thereby reducing the amount of EB that must be separated from the product stream.

Figure 2:
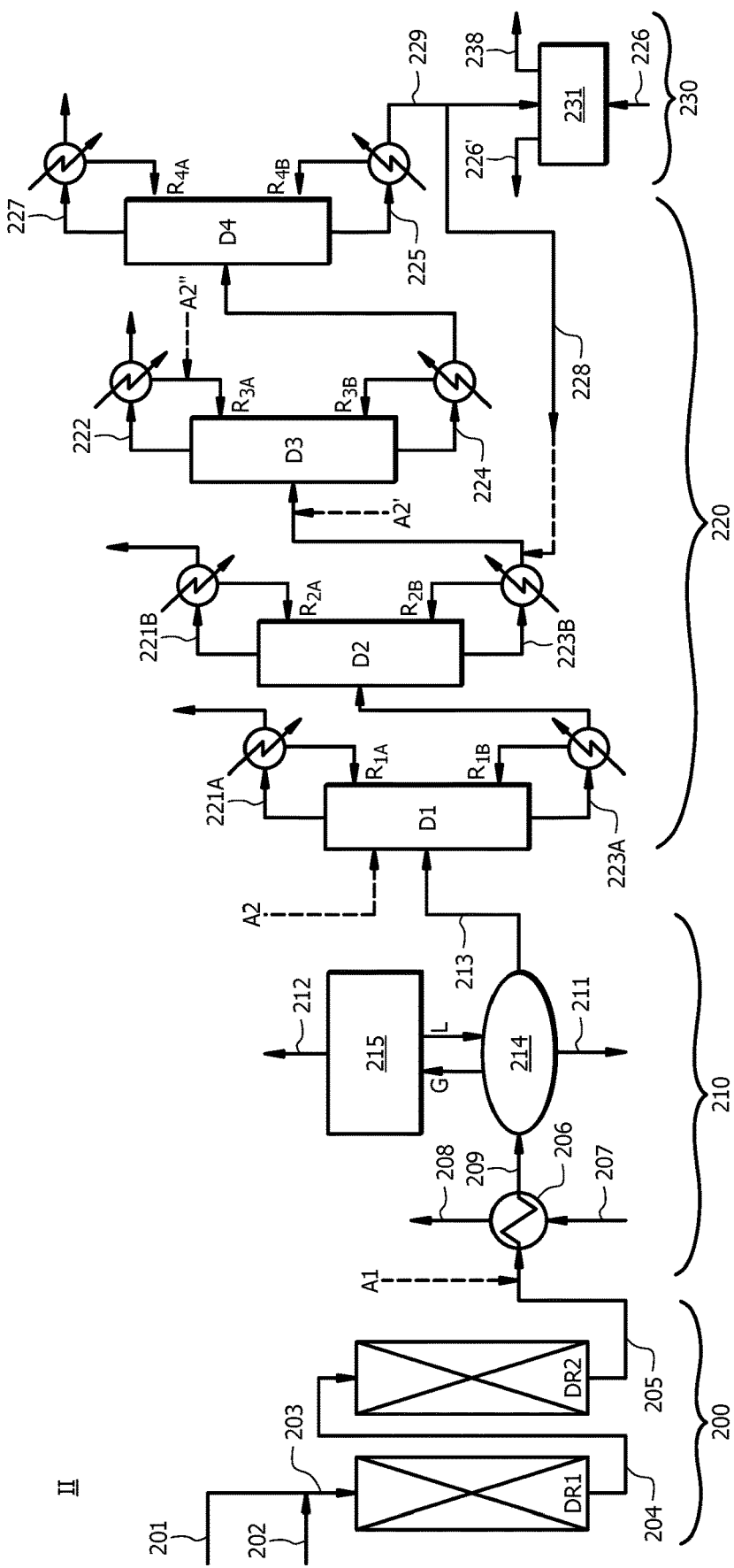
FIG. 2 is a process flow diagram of a styrene production system II according to another embodiment of this disclosure.

A styrene production system according to another embodiment of this disclosure will now be described with reference to FIG. 2, which is a process flow diagram of a styrene production system II. Styrene production system II comprises EB dehydrogenation 200, cooling, offgas, and/or condensate removal apparatus 210 (also referred to as 'condensation section 210'), styrene separation/distillation 220, and tar oxidation 230. An EB dehydrogenation system 200 according to this disclosure may comprise any number of dehydrogenation reactors in series and/or in parallel. In embodiments, EB dehydrogenation system 200 comprises three dehydrogenation reactors in series, as described above, while, in other embodiments, dehydrogenation system 200 comprises two dehydrogenation reactors in series upstream of and parallel with a downstream dehydrogenation reactor. In the embodiment of FIG. 2, the crude styrene production system comprises an EB dehydrogenation system 200, comprising a first EB dehydrogenation reactor DR1, in series with a second EB dehydrogenation reactor DR2. EB dehydrogenation reactors DR1 and DR2 are configured for the conversion of EB to styrene via dehydrogenation. During EB dehydrogenation, styrene is produced, as indicated schematically in Eq. 1 above and textually in Eq. 2 below:

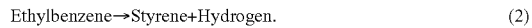
Ethylbenzene→Styrene+Hydrogen. (2)

Additionally, some benzene and toluene are produced via Eqs. 3 and 4:

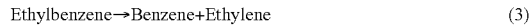
Ethylbenzene→Benzene+Ethylene (3)

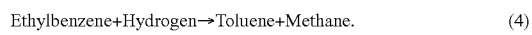
Ethylbenzene+Hydrogen→Toluene+Methane. (4)

EB in EB reactant line 201, and steam in steam reactant line 202 are combined and introduced into first EB dehydrogenation reactor DR1 via reactant feed inlet line 203. Within first EB dehydrogenation reactor DR1, EB is dehydrogenated in the presence of suitable dehydrogenation catalyst under dehydrogenation conditions, to produce styrene and hydrogen. The product of first EB dehydrogenation reactor DR1 is introduced into second EB dehydrogenation reactor DR2 via first dehydrogenation reactor outlet line 204. Within second EB dehydrogenation reactor DR2, unreacted EB (and/or EB introduced directly into second EB dehydrogenation reactor DR2 (not shown in the embodiment of FIG. 2)) is converted to styrene monomer in the presence of dehydrogenation catalyst.

Dehydrogenation reactors DR1 and DR2 may be any dehydrogenation reactors known to those of skill in the art. As noted above, three reactor systems are an equally viable option. In embodiments, dehydrogenation reactors DR1 and DR2 are adiabatic reactors. Dehydrogenation reactors DR1 and DR2 contain therein dehydrogenation catalyst suitable to catalyze the dehydrogenation of hydrocarbon in the hydrocarbon feed to dehydrogenation product. In embodiments, the dehydrogenation catalyst is a catalyst operable to dehydrogenate ethylbenzene in a hydrocarbon feed to produce a dehydrogenation product comprising styrene. Suitable dehydrogenation catalysts and conditions are known in the art, and will not be described in detail herein. For example, such conditions may include a temperature of about 600° C., a reduced pressure at the outlet of, for example, 6 PSIA (41 kPa), and a large steam dilution (e.g., 5-9 molar ratio of steam to EB). One of skill in the art will find apparent the selection of a suitable dehydrogenation catalyst based on the given reactor conditions. In embodiments, the dehydrogenation catalyst comprises iron (III) oxide, promoted by potassium oxide or potassium carbonate, rare earth oxides and other inorganic performance promoters. In embodiments, the dehydrogenation catalyst comprises a heterogeneous catalyst system suited to operate with steam dilution, reduced pressure and high temperature to overcome the equilibrium constraints and the endothermic reaction.

Crude styrene effluent of EB dehydrogenation apparatus 200 is introduced via crude styrene effluent line 205 into cooling, offgas, and/or condensate removal apparatus 210. Cooling, offgas, and/or condensate removal apparatus 210 is configured to cool the hot dehydrogenation reactor crude styrene effluent from EB dehydrogenation apparatus 200, and may also be configured to remove an offgas and/or condensate therefrom. For example, in the embodiment of FIG. 2, heat exchanger 206 is configured to reduce the temperature of the crude styrene effluent in crude styrene effluent line 205 via heat exchange with a cooling medium introduced into heat exchanger 206 via coolant inlet line 207. Cooled crude styrene is removed from heat exchanger 206 via cooled crude styrene outlet line 209, and heated heat exchange medium removed therefrom via heat exchange outlet line 208. In embodiments, a separator may be utilized to separate a gas and or condensate from the cooled crude styrene. For example, in the embodiment of FIG. 2, separator 214 is configured to separate a gas and a condensate (e.g., comprising condensed water) from the cooled crude styrene introduced thereto via cooled crude styrene outlet line 209. Gas from separator 214 may be introduced into gas compressor 215 via gas line G and compressed liquid returned to separator 214 via liquid line L. Offgas may be removed from compressor 215 via offgas outlet line 212. Condensate may be removed from separator 214 via condensate outlet line 211. An additive of this disclosure may be introduced into condensation section 210, for example into heat exchanger 206 via one or more additive inlet lines A1.

Cooled crude styrene from which offgas and/or condensate may have been removed can be introduced into styrene separation/distillation apparatus 220 (also referred to herein as styrene purification apparatus 220) via separations or 'dehydrogenation mixture' or 'DM' feed line 213. Styrene purification apparatus 220 can comprise any suitable number of distillation columns, as known in the art. Generally, the separations system is operable to separate one or more byproducts (e.g., benzene and/or toluene), unreacted reactant (e.g., EB) and heavy residue (also referred to herein as 'tar') to provide a purified styrene monomer stream. In embodiments, styrene separation system 220 comprises one or more distillation columns configured for the separation of a tops product comprising benzene and toluene from a bottoms product comprising EB and styrene, one or more distillation columns configured for the separation of a tops product comprising benzene from a bottoms product comprising toluene, EB and styrene, one or more distillation columns configured for the separation of a tops product comprising toluene from a bottoms product comprising EB and styrene, one or more distillation columns configured for the separation of a tops product comprising EB from a bottoms product comprising styrene, one or more distillation columns configured for the separation of a tops product comprising styrene from a bottoms product comprising tar, or a combination thereof.

Styrene separation/distillation apparatus 220 of the embodiment of FIG. 2 comprises four distillation columns, including first distillation column D1, second distillation column D2, third distillation column D3, and fourth distillation column D4. First distillation column D1 is configured for the separation of the cooled crude styrene introduced thereto via separations or DM feed line 213 into a tops product comprising benzene (which is removed therefrom via benzene outlet line 221A) and a bottoms product comprising toluene, EB and styrene (which is removed therefrom via first distillation column bottoms product outlet line 223A). Second distillation column D2 is configured for the separation of the first distillation column bottoms product introduced thereto via first distillation column bottoms product outlet line 223A) into a tops product comprising toluene (which is removed therefrom via toluene outlet line 221B and a bottoms product comprising styrene and EB (which is removed therefrom via second distillation column bottoms outlet line 223B. As noted herein, first and second distillation columns D1 and D2, in embodiments, can be combined in a single column operable to remove a mixed stream of benzene and toluene overhead, as depicted in the embodiment of FIG. 3, detailed hereinbelow. Third distillation column D3 is configured for the separation of the second distillation column bottoms product introduced thereto via second distillation column bottoms product outlet line 223B into a tops product comprising EB (which is removed therefrom via EB outlet line 222 and a bottoms product comprising styrene (which is removed therefrom via third distillation column bottoms outlet line 224. Fourth distillation column D4 is configured for the separation of the third distillation bottoms product introduced thereto via third distillation column bottoms product outlet line 224 into a tops product comprising styrene monomer (which is removed therefrom via purified styrene outlet line 227 and a bottoms product comprising tar (which is removed therefrom via fourth distillation column bottoms or 'tar' outlet line 225). All or a portion of the styrene/tar in tar outlet line 225 can be recycled and/or sent for further processing via a recycle and/or further processing line 228 (depicted in FIG. 2 as a recycle line fluidly connecting fourth distillation column bottoms product line 225 with second distillation column bottoms product line 228, whereby styrene/tar can be recycled to third distillation column D3. Optionally, as noted hereinbelow, additional styrene finishing columns may be employed to remove latent monomer from the tar stream.

A styrene production system according to another embodiment of this disclosure will now be described with reference to FIG. 3, which is a process flow diagram of a styrene production system III. Styrene production system III comprises EB dehydrogenation section 300 comprising x (e.g., one or more) EB dehydrogenation reactors DRx, cooling, offgas, and/or condensate removal apparatus 310 (or "condensation section" 310) from which offgas 312 and DM feed 313 are obtained, and styrene separation/distillation 320. Styrene separation/distillation apparatus 320 of the embodiment of FIG. 3 comprises three distillation columns, including first distillation column D1, second distillation column D2, and third distillation column D3. In this embodiment, first distillation column D1 is configured for the separation of the cooled crude styrene introduced thereto via separations or DM feed line 313 into a tops product comprising benzene and toluene (which is removed therefrom via benzene outlet line 321) and a bottoms product comprising EB and styrene (which is removed therefrom via first distillation column bottoms product outlet line 323). Second distillation column D2 is configured for the separation of the first distillation column bottoms product introduced thereto via first distillation column bottoms product outlet line 323 into a tops product comprising EB (which is removed therefrom via EB outlet line 322 and a bottoms product comprising styrene (which is removed therefrom via third distillation column bottoms product outlet line 324. Third distillation column D3 is configured for the separation of the second distillation bottoms product introduced thereto via second distillation column bottoms product outlet line 324 into a tops product comprising styrene monomer (which is removed therefrom via purified styrene outlet line 327 and a bottoms product comprising tar (which is removed therefrom via fourth distillation column bottoms or 'tar' outlet line 325). Optionally, additional styrene finishing columns, as described below, may be employed to remove latent monomer from the styrene/tar stream in tar outlet line 325.

A distillation column configured for the removal of EB as a tops product (e.g., third distillation column D3 of the embodiment of FIG. 2 and second distillation column D2 of the embodiment of FIG. 3) may be referred to as an "EB recycle column". A distillation column configured for the removal of styrene monomer (SM) as a tops product (e.g., fourth distillation column D4 of the embodiment of FIG. 2 and third distillation column D3 of the embodiment of FIG. 3) may be referred to as a "styrene finishing column". A styrene production system of this disclosure can comprise one or more EB recycle columns and one or more SM finishing columns, for example, in series and/or parallel.

In embodiments according to this disclosure, an IPAA or IPAC may be introduced into or with a feed, recycle, and/or reflux stream to a distillation column downstream of an EB dehydrogenation reactor. For example, an additive inlet line A2 may be configured for the introduction of IPAA or IPAC into a first distillation column D1 of separation section 120/220/320 separately from or in combination with the cooled crude styrene in DM feed line 213/313. Alternatively or additionally, an IPAA or IPAC of this disclosure can be introduced into a reflux line of one of the distillation columns, for example, in embodiments, an IPAA or IPAC of this disclosure can be introduced into tops reflux R1A and/or bottoms reflux R1B of first distillation column D1, into tops reflux R2A and/or bottoms reflux R2B of second distillation column D2, into tops reflux R3A and/or bottoms reflux R3B of third distillation column D3, and/or into tops reflux R4A and/or bottoms reflux R4B of fourth distillation column D4.

In embodiments, IPAA or IPAC is introduced into an EB recycle column and/or a styrene finishing column. By way of example, in the embodiments of FIG. 2 and FIG. 3, an additive inlet line A2' is configured for the introduction of an IPAA or IPAC according to this disclosure into the EB recycle column (e.g., distillation column D3 in the embodiment of FIG. 2 and distillation column D2 in the embodiment of FIG. 3) (configured for the separation of a tops product comprising EB from a bottoms product comprising styrene) via introduction into the bottoms product of the immediately upstream distillation column (e.g., bottoms product in bottoms product outlet line 223B of second distillation column D2 of the embodiment of FIG. 2 or bottoms product in bottoms product outlet line 323 of first distillation column D1 of the embodiment of FIG. 3). Although not shown in the embodiment of FIG. 2 or FIG. 3, the additive inlet line A2' can introduce the IPAA or IPAC directly into the EB recycle column, in embodiments. By way of further example, as depicted in the embodiment of FIG. 2, an additive inlet line A2" can be configured for the introduction of an IPAA or IPAC according to this disclosure into the EB recycle column (e.g., the third distillation column D3 in the embodiment of FIG. 2), configured for the separation of a tops product comprising EB from a bottoms product comprising styrene (e.g., via introduction into the tops reflux introduced thereto via tops reflux line R3A in the embodiment of FIG. 2). As will be apparent to those of skill in the art on reading this disclosure, the injection point for IPAA and IPAC can be anywhere in the separating system and can vary based upon specific plant designs and particular point of fouling in individual production plants.

As discussed hereinabove with reference to the embodiment of FIG. 1, a styrene production system according to this disclosure may further comprise oxidation apparatus configured to oxidize at least one component of a tar stream comprising styrene (also referred to herein as a styrene/tar stream) introduced thereto and thus provide one or more IPAAs of this disclosure. With reference to FIG. 2, oxidation section 230 comprises oxidation reactor(s) 231 configured to oxidize at least one component of the tar introduced thereto via fourth distillation column outlet line 225 and tar oxidation feed line 229. Oxidation apparatus 231 may be configured to produce at least one oxygenated chemical component that is an IPAA suitable for use in insoluble polymer abatement as per this disclosure, which IPAA(s) can be used as is in the liquid effluent 238 or the liquid effluent comprising the IPAA(s) can be removed from tar removal apparatus 230 via liquid effluent line 238. Liquid effluent line 238 may fluidly connect tar oxidation apparatus 231 with an upstream apparatus whereby the oxygenated chemical component IPAA produced within oxidation apparatus 230 can be introduced into an upstream apparatus alone or as part of an IPAC. For example, liquid effluent line 238 can be fluidly connected with additive inlet line A1, additive inlet line A2', and/or additive inlet line A2", described hereinabove. Alternatively, as noted above with reference to the embodiment of FIG. 1, oxidation apparatus 231 may be positioned at another location within separation system 220 as desired, and the oxidation product comprising IPAAs in liquid effluent line 238 recycled to any suitable point in the separation section 220.

Figure 3:
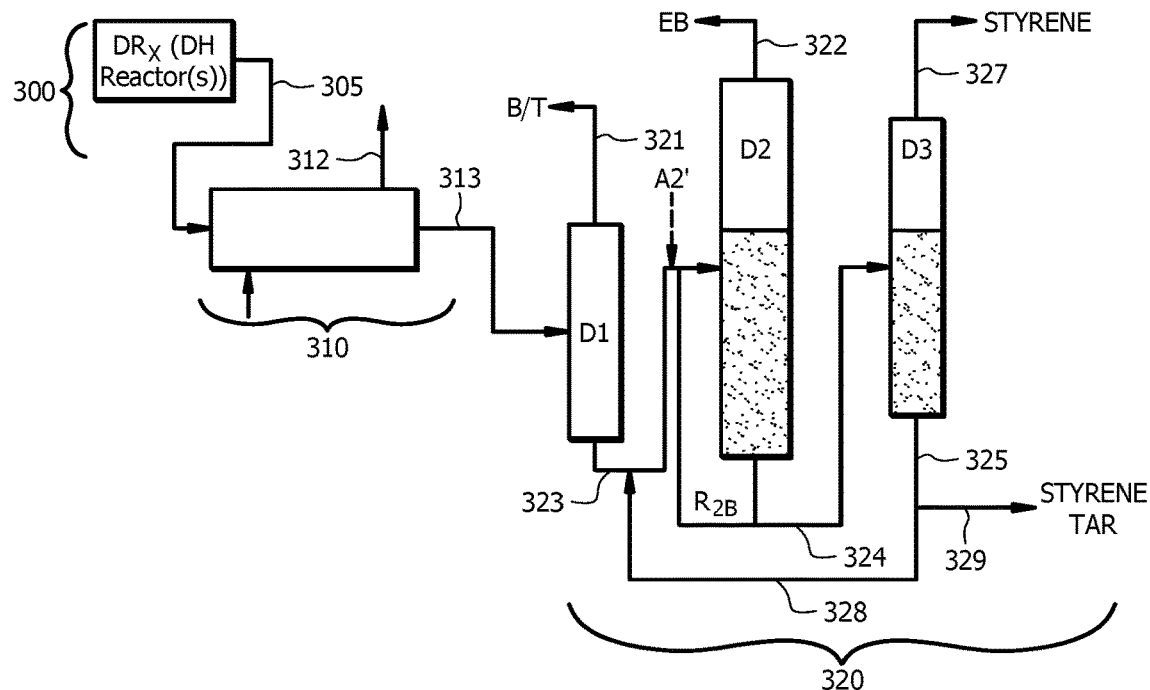
FIG. 3 is a process flow diagram of a styrene production system III according to another embodiment of this disclosure.

Although possible arrangements of distillation columns are depicted in the embodiments of FIG. 2 and FIG. 3, one will appreciate that other combinations and/or orders of distillation columns can be utilized to separate the styrene monomer from the crude styrene, and such alternative arrangements are included in the scope of this disclosure. For example, the styrene separation/distillation section of FIG. 3 comprises a first distillation column configured to separate a tops product comprising toluene, and benzene, from a bottoms product comprising EB and styrene, a second distillation column configured to separate the bottoms product comprising EB and styrene from the first distillation column into a tops product comprising EB (which may be recycled to the EB dehydrogenation section) and a bottoms product comprising styrene and tar, and a third distillation column configured to separate the bottoms product comprising styrene and tar from the second distillation column into a tops product comprising styrene monomer and a bottoms product comprising tar. In such an embodiment, an additive according to this disclosure may be added to the feed, recycle, and/or reflux to any combination of the distillation columns, for example, to a crude styrene feed to the first distillation column and/or to a reflux to the second distillation column. In other embodiments, multiple distillation columns may be utilized to effect a given separation. By way of nonlimiting example, in embodiments multiple distillation columns are employed to effect the separation of a crude styrene stream from which benzene, toluene and EB have been removed into a purified styrene monomer product and a tar stream (i.e., to separate styrene from tar). Furthermore, various other components (e.g., heaters) may be employed in the system as known in the art (e.g., to maintain a flowable tar). Other arrangements are suitable, and will be readily apparent to those of skill in the art.

As noted above, an IPAA or IPAC according to this disclosure introduced within the first area (i.e., the area where gas phase crude styrene from styrene production reactors is first condensed to liquid) via an additive inlet line A1 may be different from an IPAA or IPAC introduced into the second area (i.e., in the distillation columns of downstream separations/purification apparatus where DVB vapor could condense without the presence of inhibitor/retarder) via an additive line A2, which may itself be the same or different from an IPAA or IPAC introduced elsewhere (e.g., into a tar recycle stream) via an additive inlet line A3. The conditions at these locations can be different, thus making one or another of the herein disclosed IPAAs more beneficial in a particular area. For example, the condensate zone can have a higher temperature, lower styrene monomer concentration, and steam, while the distillation column reflux areas can have lower temperatures, higher styrene monomer concentrations, and higher DVB concentrations.

In embodiments, an IPAC comprising IPAA including benzaldehyde and/or acetophenone and produced by oxidation of styrene tar as described herein further comprises an IPAA produced otherwise. By way of example, an IPAA introduced into the first area (e.g., via additive inlet line A1) may comprise a higher boiling point chemical component(s) and/or different chemical reactivity (i.e., different functional group(s)) than an IPAA introduced into the second area (e.g., via an additive inlet line A2, A2', A2"). Similarly, an IPAA introduced into the first area (e.g., via additive inlet line A1) and/or the second area (e.g., via an additive inlet line A2, A2', A2") may comprise a lower boiling point chemical component(s) and/or different chemical reactivity than an IPAA introduced into the third area (e.g., via an additive inlet line A3). By way of nonlimiting example, benzoates may be more suitable for use as an additive or additive component of an IPAC for introduction into the second area, but may not be well suited for use in the first area due to dissociation in the presence of steam.

In embodiments, an IPAA or IPAC is injected into the cooling, offgas, and/or or condensate removal apparatus 110/210 (e.g., via additive line A1) to inhibit or prevent the initiation of insoluble polymer formation due to DVB liquefaction and initiation. Such IPAA or IPAC can be injected neat or as a solution in dosages from 1 to 1000 ppm (0.0001 to 0.1 wt %) relative to the organic portion of the process stream. Without limitation, in such embodiments, the IPAC may comprise one or more components selected from: phenylethanol, terpineol, propylene glycol, ethyl carbamate, acetophenone biphenyl, benzaldehyde, tetralin, diethanolamine, 3-amino-1-propanol, or combinations thereof. In embodiments, an IPAA introduced into the first area exhibits effective function at higher temperatures, unperturbed by steam, suitable reactivity for condensate conditions, or a combination thereof.

In embodiments, an IPAA or IPAC is injected into the feed to or any column of the separation section or apparatus 120/220 (e.g., via additive inlet line(s) A2, A2', A2", or elsewhere) to prevent the initiation of insoluble polymer formation due to DVB liquefaction and initiation. Such IPAA or IPAC can be injected neat or as a solution in dosages from 1 to 1000 ppm (0.0001 to 0.1 wt %) relative to the organic portion of the process stream. Without limitation, in such embodiments, the IPAC may comprise one or more components selected from: propylene glycol, dipropylene glycol, methyl benzoate, benzaldehyde, diethylaminoethanol, acetophenone, DPGME (dipropyleneglycol methyl ether), tetralin, ethylacetoacetate, terpineol, biphenyl, or combinations thereof. In embodiments, an additive introduced into the second area provides suitable boiling point, reactivity sufficient for high styrene/DVB concentrations, acceptable physical properties, or a combination thereof.

In embodiments, an IPAA or IPAC introduced into the third area via additive inlet line A3 comprises the properties appropriate for its injection point back to the system.

In embodiments, an IPAA is prepared (partially or wholly) from styrene tar or crude styrene streams comprising suitable oxidizable components via a tar oxidation unit 130/230/330. The oxidized stream (e.g., in liquid effluent line 138) can contain mixtures of oxidation products from components in the tar or crude streams in concentrations from about 10 ppm to 100,000 ppm (0.001 to 10 wt %), including one or more IPAAs. In embodiments, the IPAA(s) in the oxidized stream can be injected to the feed stream 113/213/313 to the separation section 120/220/320 or any point therein. Without limitation, in such embodiments, the IPAA may be selected from: acetophenone, benzaldehyde, phenylethanol, or combinations thereof.

Oxidation Catalyst

Also disclosed herein is an oxidation catalyst for the aerobic oxidation of styrene to benzaldehyde and acetophenone. The oxidation catalyst can comprise one or more metal ions that activate molecular oxygen, such as, without limitation, cobalt (Co), manganese (Mn), iron (Fe), molybdenum (Mo), or combinations thereof. Due to the high concentrations of polymer and heavy molecules in styrene process streams that may, in embodiments, be oxidized in the presence of the aerobic oxidation catalyst of this disclosure, the oxidation catalyst can comprise a catalyst support having robust character, lower surface area and/or large pores, as detailed hereinbelow.

The oxidation catalyst of this disclosure comprises a porous support, and an active phase comprising an oxygen activation metal comprising cobalt (Co), manganese (Mn), iron (Fe), molybdenum (Mo), or a combination thereof. In embodiments, the oxygen activation metal comprises cobalt (Co) or manganese (Mn). In embodiments, the oxidation catalyst comprises from about 0.2 to about 4, from about 0.5 to about 3.5, or from about 0.5 to about 2 weight percent (wt %) of the active phase, based on the total weight of the oxidation catalyst and the weight of the appropriate oxide form of the active phase after calcining. In embodiments, the active phase (after calcining) comprises cobalt (III) oxide ($Ca_2O_3$) or manganese (IV) oxide ($Mn_2O_3/MnO_2$). In embodiments, the oxidation catalyst thus comprises cobalt oxide or manganese oxide on a macroporous alumina or silica/alumina support, as described herein.

In embodiments, the support is a low surface area support having a Brunauer Emmett and Teller (BET) surface area, determined by ASTM D3663, that is less than or equal to 20, 15, or 10 $m^2/g$ and/or greater than or equal to 0.001, 0.005, or 0.01 $m^2/g$. In embodiments, the support comprises alumina, alumina-silica or a combination thereof. In embodiments, the support comprises from about from about 0 to about 25, from about 0 to about 10, from about 0 to about 1, from about 1 to about 10, from about 10 to about 25 weight percent (wt %), or less than or equal to about 33, 30, 25, 20, 15, 10, 9, 8, 7, 6, 5, 4, 3, 2, or 1 wt % silica. The use of such a chemically inert support can help maintain the activity of the active phase. In embodiments, the support is a macroporous support. As utilized herein, a macroporous support comprising pores having an average pore size of greater than or equal to about 50, 60, 70, 75, 80, 90, or 100 microns (p). In embodiments, the macroporous support comprises pores having an average pore size of less than or equal to about 40, 50, 60, 70, or 80 microns (p). In embodiments, the catalyst/catalyst support has a liquid pore volume, as measured by gravimetric water absorption, that is greater than or equal to about 0.1 to 0.3 mL/g (e.g., greater than or equal to about 0.1, 0.2, or 0.3 mL/g. The support can be any shape, for example, without limitation, spherical, cylindrical, tabletized or a combination thereof. Without limitation, in embodiments, the support has an average largest dimension (e.g., an average diameter of a spherical support) that is in a range of from about 1 to about 5, from about 1 to about 4, from about 1 to about 3 mm, less than or equal to about 5, 4.5, 4, 3, 2, or 1 mm, and/or greater than or equal to about 0.1, 1, 2, 3, or 4 mm. In embodiments, the support comprises low surface area, macroporous alumina or silica-alumina spheres.

Also disclosed herein is a method of producing an oxidation catalyst of this disclosure. The method comprises forming an aqueous solution of an active metal precursor, wherein the active metal comprises cobalt (Co), manganese (Mn), iron (Fe), molybdenum (Mo), or a combination thereof, impregnating a support with the aqueous solution to form an impregnated support, and calcining to form the oxidation catalyst. In embodiments, the active metal precursor comprises cobalt(III)nitrate hexahydrate, manganese(II) nitrate, iron(III)nitrate nonahydrate, ammonium heptamolybdate tetrahydrate, or an analogous water soluble salt thereof, or a combination thereof. Impregnating can comprise incipient wetness impregnation (also known as IW, IWI, capillary impregnation, or dry impregnation). In embodiments, calcining comprises calcining in air. Calcining can comprise heating the impregnated support at a temperature of less than or equal to about 200° C., heating the impregnated support at a temperature of greater than or equal to about 200° C. and less than or equal to about 300° C., heating the impregnated support at a temperature of greater than or equal to about 300° C. and less than or equal to about 400° C., or a combination thereof.

In embodiments, the method of producing the oxidation catalyst further comprises drying the impregnated support prior to calcining. Drying can be performed via any method known to one of skill in the art. For example, in embodiments, drying comprises heating at a temperature in the range of from about 125 to about 250° C., from about 100 to about 250° C., from about 150 to about 200° C., or less than or equal to about 250, 200, 175° C., or 150° C.

As noted above, in embodiments, the support comprises alumina or silica/alumina; the support has a Brunauer Emmett Teller (BET) surface area, as determined by ASTM D3663, that is less than or equal to about 10, 9, 8, 7, 6, 5, 4, 3, 2, or 1 $m^2/g$ and/or greater than or equal to about 0.005, 0.01, or 0.1 $m^2/g$; the support is a macroporous support comprising pores having an average pore size of greater than or equal to about 50, 60, 70, 75, 80, 90, or 100 micron (p) and/or less than or equal to about 200, 175, 150, 125, or 100 micron (p); and/or the support has a liquid pore volume, as measured by gravimetric water absorption, that is greater than or equal to about 0.1, 0.16, or 0.22 mL/g, or in the range of from about 0.1 to about 0.5, from about 0.1 to about 0.4, or from about 0.1 to about 0.3 mL/g.

Method of Forming Oxidation Product

Also disclosed herein is a method of forming an oxidation product comprising benzaldehyde and acetophenone, which method will be described with reference to FIG. 4, which is a schematic of an oxidation system IV according to an embodiment of this disclosure. The method comprising: contacting the oxidation catalyst of this disclosure with styrene and air in an oxidation reactor 431 comprising the oxidation catalyst 460. The contacting can be effected at mild conditions, which can comprise a pressure of greater than or equal to atmospheric pressure and less than a pressure of 1, 3 or 5 atm, and/or a temperature in the range of from about 110 to about 130° C., or less than or equal to about 140° C., 130° C., or 120° C. The maximum operable pressure can be determined as a highest temperature that is below the lower explosive limit (LEL) of air and styrene vapors and/or below the styrene thermal self-initiation temperature. Mild conditions are desirable because of the flammability and the thermal initiation of polymerization that is possible with styrene. To ensure maximum productivity at the lowest temperatures, an oxidation catalyst as described herein can be utilized. In embodiments, the tar oxidation is effected at a temperature in the range of from about 90 to about 120° C. to avoid unwanted polymerization. These temperatures can be utilized with a liquid phase process with air injection over a heterogeneous oxidation catalyst of this disclosure.

The oxidation reactor 431 can be a batch reactor or a continuous reactor. In embodiments, such as depicted in FIG. 4, the oxidation reactor 431 is a continuous reactor, and the method further comprises introducing air 426 and a stream comprising the styrene 425 into the oxidation reactor 431. The air can be introduced into the oxidation reactor via a distributor 450, in embodiments. In embodiments, such as depicted in the embodiment of FIG. 4, the air 426 and the stream comprising the styrene 425 are introduced into the oxidation reactor 431 concurrently. In embodiments, the oxidation reactor is a concurrent upflow reactor (e.g., a concurrent upflow tubular reactor). The oxidation reactor can be a three-phase reactor comprising solid oxidation catalyst as described herein, air gaseous phase, and styrene-containing stream liquid phase.

The method of forming the oxidation product comprising benzaldehyde and acetophenone can further comprise introducing the air 426 at a gas hourly space velocity (GHSV) of greater than or equal to about 40, 30, or 20 $h^{-1}$, introducing the stream comprising styrene 425 at a liquid hourly space velocity (LHSV) of less than or equal to about 0.4, 0.3, or 0.2 $h^{-1}$, or a combination thereof. In embodiments, the method of forming the oxidation product comprising benzaldehyde and acetophenone further comprises introducing the air at a gas hourly space velocity (GHSV) and introducing the stream comprising styrene at a liquid hourly space velocity (LHSV) such that a ratio of the gas hourly space velocity to the liquid hourly space velocity (GHSV/LHSV) is greater than or equal to about 60, 70, 80, 90, 100, 110, 120, 130, 140, 150, 160, or 170.

As depicted in Example 4 hereinbelow, the air distribution in the catalyst bed can be optimized to maximize IPAA production in the oxidation reactor. As air distribution is important, a larger oxidation reactor with a distributor (e.g., distributor 450 in FIG. 4) may be more efficient for providing better air coverage throughout the entire catalyst bed within the oxidation reactor (e.g., oxidation reactor 431 of FIG. 4). Better air distribution may improve production of IPAAs in the oxidation reactor.

The stream comprising styrene can be a portion of a styrene containing stream 425 of a styrene production system (e.g., styrene production system I/II/III). For example, in embodiments, the styrene containing stream 425 can comprise a portion of a styrene/tar stream from a styrene finishing column of a styrene production plant (e.g., oxidation feed stream in oxidation feed line 129 from the tar stream in tar stream line 125 of FIG. 1, oxidation feed stream in oxidation feed line 229 from the tar stream in tar stream line 225, 224, 223B and/or 223A of FIG. 2, oxidation feed stream in oxidation feed line 329 from the tar stream in tar stream line 325, 324 or 323 of FIG. 3). In embodiments, the tar stream is a portion of a bottoms product of a (e.g., first) styrene finishing column (e.g., styrene finishing distillation column D4 of the embodiment of FIG. 2 or styrene finishing column D3, D2 or D1 of the embodiment of FIG. 3) of a styrene separation section 120/220/320 of the styrene production system or plant. Alternatively or additionally, styrene containing stream 425 comprises styrene in styrene monomer stream 127/227/327, and/or another styrene containing stream elsewhere in the styrene production system I/II/III. For example, in embodiments, the styrene containing stream 425 comprises a bottoms product from a second styrene finishing column downstream of a first styrene finishing column (e.g., a second styrene finishing column downstream of styrene finishing distillation column D4 of the embodiment of FIG. 2 or a second styrene finishing column downstream of styrene finishing column D3 of the embodiment of FIG. 3).

In embodiments, the stream comprising styrene introduced into oxidation reactor 431 comprises from about 25 to about 99.9, or greater than or equal to about 80, 85, 90, or 98 weight percent (wt %) styrene. The stream comprising styrene (e.g., a styrene/tar stream) introduced into oxidation reactor 431 can further comprise one or more polymerization inhibitors, components heavier than styrene (e.g., polymers, or a combination thereof. In embodiments, the oxidation process is operable in the presence of such styrene process stream components or byproducts and may not impair the polymerization retarder (e.g., DNBP retarder) present in the styrene tar stream, which can thus be recycled to the separation section I/II/III along with the IPAA produced in the oxidation reactor.

The liquid effluent comprising oxidation products can be removed via liquid effluent line 438. Effluent line 438 may then be introduced to the separating section 120 to supply IPAA/IPAC. Effluent line 438 (138) may be fluidly connected with a storage vessel for storage of the liquid effluent from oxidation reactor 431 (or oxidation section 130 or 431). In embodiments, the liquid effluent in liquid effluent line 438 can comprise about 1, 1.5, or 2 wt % IPAAs or more.

Tar Oxidation Section

As noted hereinabove, a styrene production system (e.g., styrene production system I of FIG. 1, styrene production system II of FIG. 2, and styrene production system III of FIG. 3) can comprise a tar oxidation section (e.g., tar oxidation section 130 of FIG. 1, tar oxidation section 230 of FIG. 2, and tar oxidation section 330 of FIG. 3). A tar oxidation section 130/230/330 of this disclosure can comprise an oxidation catalyst of this disclosure, as detailed hereinabove. A tar oxidation section 130/230/330 of this disclosure can comprise an oxidation reactor of this disclosure (e.g., oxidation reactor 231 of FIG. 2, which may be an oxidation reactor 431 as described with reference to FIG. 4), as detailed hereinabove. The tar oxidation section 130/230/330 can be operable for forming an oxidation product comprising one or more IPAAs, as described hereinabove with reference to FIG. 4. As depicted in FIG. 2 and FIG. 3, in embodiments, a portion 229/329 of the tar stream 225/325 can be introduced into oxidation reactor 231/431 of oxidation section 230/330, and a liquid effluent 238/338 comprising oxidation products including benzaldehyde and acetophenone removed therefrom. Excess air can be removed via excess air line 226'326'. All or a portion of the liquid effluent 238/338 can be utilized directly as the IPAC, in embodiments.

In embodiments, the oxidation reactor utilized to produce IPAA(s) from styrene plant process stream(s) can be operated as an off-line operation by removing some of a process stream from which the IPAAs are to be produced, conducting the oxidation and then returning it back to the styrene production process. As conventional EB dehydrogenation processes, reactors and distillation columns are operated at reduced pressure, and the oxidation reactor utilizes, at a minimum, ambient pressures with an excess of air, the oxidation is not suitable for an in-line unit operation, in such embodiments. In embodiments, an oxidation reactor utilized in a styrene production process of this disclosure for the production of IPAAs is relatively small (e.g., relative to the size of the distillation columns of the separation section 120/220/320) because the DVB concentration is low such that the production of the equivalent or near equivalent amount of IPAA(s) will not require a large oxidation unit.

In embodiments, a styrene oxidation reactor, such as described with reference to FIG. 4, can be placed in the styrene production system I/II/III to produce oxidation products comprising the IPAAs benzaldehyde and acetophenone from selected plant streams for subsequent recycling back to (e.g., the front end) of the styrene purification section 120/220/320 to provide insoluble polymer abatement within the styrene production system.

Method of Reducing Fouling in Styrene Production Process

A method of reducing the fouling in a process for the production of styrene according to this disclosure can comprise: producing, via oxidation of a crude styrene stream, a tar stream comprising styrene, or a combination thereof, an oxidation product comprising benzaldehyde, acetophenone, or a combination thereof, wherein the oxidation is effected with the oxidation catalyst of this disclosure; and introducing an additive stream comprising at least a portion of the oxidation product into a stream comprising styrene and byproduct divinyl benzene (DVB), whereby divinyl benzene (DVB) crosslinking is inhibited. As detailed in Example 1 herein below, benzaldehyde appears to consume DVB, and thus not only inhibit polymer formation but also show a large reduction in DVB concentration. Accordingly, benzaldehyde may be a superior IPAA, in embodiments. According to this disclosure, the IPAAs benzaldehyde and acetophenone can be prepared via aerobic oxidation from styrene-containing process streams and added back into the process to suppress insoluble polymer fouling. In embodiments, the aerobic oxidation process, as described hereinabove, is mild in view of the reactivity of styrene but productive enough to produce the desired total amounts of IPAA. Desirably, IPAA production in oxidation section 130/230/330 matches the DVB concentrations in the styrene process streams to be treated with the additive (e.g., into which the IPAA(s) or an IPAc comprising the IPAA(s) is introduced).

In embodiments, the tar stream comprising styrene is a slip stream of a bottoms stream from a styrene finishing column configured to separate the bottoms stream from an ethylbenzene (EB) recycle column into a bottoms stream comprising the tar stream and an overhead stream comprising styrene. The slip stream can comprise less than or equal to about 1, 5, 10, 15, or 20 weight percent (wt %) of the bottoms stream from the styrene finishing column, in embodiments. That is, in embodiments, the weight percentage of the oxidation feed stream in oxidation feed line 129 to the tar stream in tar line 125, the weight percentage of the oxidation feed stream in oxidation feed line 229 to the tar stream in tar line 225, or the weight percentage of the oxidation feed stream in oxidation feed line 329 to the tar stream in tar line 325 can be less than or equal to about 1, 5, 10, 15, or 20 weight percent (wt %).

In embodiments, the additive stream is introduced into the stream comprising styrene and DVB such that a concentration of benzaldehyde, a concentration of acetophenone, or a sum of the concentration of benzaldehyde and the concentration of acetophenone is greater than or equal to about 0.001, 0.01 or 0.1 or in a range of from about 0.001 to about 0.1, from about 0.01 to about 0.1, or from about 0.001 to about 0.2 weight percent of the stream. As described hereinabove, the stream comprising styrene and DVB into which the additive stream is introduced can be a feed, recycle, or reflux stream to a distillation column downstream of an EB production (e.g., dehydrogenation) reactor. For example, in embodiments, the distillation column comprises an EB recycle distillation column configured for the separation of a tops product comprising EB from a bottoms product comprising styrene, a distillation column configured for the separation of a tops product comprising benzene and toluene from a bottoms product comprising EB and styrene, or a styrene finishing distillation column configured for the separation of a tops product comprising styrene from a bottoms product comprising tar and styrene. In embodiments, reducing the fouling comprises a reduction in the formation of insoluble polystyrene, soluble polystyrene, or both, of at least 1, 10, 50, or 100% relative to the same process absent the additive stream. The additive stream can further comprise a polymerization inhibitor having a boiling point of above 195° C., 200° C., 250° C., or 300° C. As described hereinabove, such a polymerization inhibitor can be selected from dinitrophenols, quinone derivatives, TMPO compounds (e.g., 4-hydroxy-2,2,6,6-tetramethylpiperidine 1-oxyl), oximes, or a combination thereof, in embodiments.

The oxidation product can be formed via the method of forming an oxidation product described herein. In embodiments, an oxidation catalyst of this disclosure is utilized for the aerobic oxidation of a styrene process stream (e.g., a fraction of a styrene finishing column bottoms product stream) for the production of IPAAs (e.g., benzaldehyde and acetophenone) at production rates sufficient for the on-site production of sufficient amounts of one or more IPAAs for typical DVB concentrations in the plant. In embodiments, sufficient amounts comprise an amount (e.g., a wt/o) of IPAA(s) substantially equal to or about 1, 2, 3, 4, or 5 times (and/or 1, 2, 3, 4, or 5 wt %) greater than an amount (e.g., a wt %) of DVB in a process stream into which the IPAAs that are formed are subsequently introduced for insoluble polymer abatement.

The identification of a styrene process stream to utilize for the production of the oxidation product comprising IPAAs including benzaldehyde and acetophenone can be based on styrene concentration, anti-polymerization concentration and viscosity of the styrene process stream. For example, in embodiments, a source for the oxidation feed stream (129/229/329) is the bottoms stream from the first styrene separation or finishing column, such as third distillation column D3 of the embodiment of FIG. 2 and second distillation D2 of the embodiment of FIG. 3. This stream can have a high styrene concentration (e.g., greater than or equal to about 80, 90, 95, or 98 wt %) and a high anti-polymerization concentration (e.g., greater than or equal to about 200, 800, 1400 or 2000 ppm wt/wt) with low overall viscosity; and can have a temperature in a range of 85 to 100, or 85 to 110° C. The presence of the anti-polymerization additive can be important in order to conduct the oxidation above 80° C., where thermal initiation of styrene occurs at significant rates. In embodiments, the remainder of the stream (e.g., the 5, 10, or 20 wt % non-styrene portion) comprises heavies, polymer and/or anti-polymerization additives.

Also disclosed herein is a system (e.g., styrene production system/I/III of FIG. 1/2/3) for the production of styrene via dehydrogenation of ethylbenzene (EB). The system comprises one or more dehydrogenation reactors operable to contact EB and steam with a dehydrogenation catalyst under dehydrogenation conditions to yield a crude styrene effluent 105/205/305 comprising styrene and byproduct divinyl benzene (DVB); a heat exchange apparatus (206 FIG. 2) configured to reduce the temperature of the crude styrene effluent; a separations apparatus (214 FIG. 2) configured to separate an offgas 112/212/312 and/or a condensate 111/211 from the cooled crude styrene effluent and thus provide a dehydrogenation mixture 113/213/313; a distillation section 120/220/320 operable to separate the dehydrogenation mixture into one or more streams comprising benzene, toluene, ethylbenzene, or a combination thereof, a tar stream 125/225/325 comprising tar and styrene, and a stream comprising styrene 127/227/327; an oxidation unit 130/230/330 configured to produce, via oxidation of a portion of the tar stream, an oxidation product stream 138/238/338 comprising oxidation products including benzaldehyde, acetophenone, or a combination thereof, wherein the oxidation unit 130/230/330 comprises the oxidation catalyst of this disclosure; and one or more recycle lines whereby at least a portion of the oxidation product stream, can be combined with the crude styrene effluent, the cooled crude styrene effluent, the dehydrogenation mixture, a feed, recycle, or reflux to a distillation column of the distillation section 120/220/320, or a combination thereof. The recycle line can connect, for example, a liquid effluent line from the oxidation reactor (e.g., liquid effluent line 138/238/338) with an additive inlet line (e.g., A1, A2', A2") as described hereinabove.

Features/Potential Advantages of the Herein-Disclosed Additive, Composition, System, and Method Several possible insoluble polymer abatement additives have been identified herein, and, as insoluble polymer fouling in styrene production plants is a common problem, such IPAAs can be utilized to reduce fouling in styrene production plants. As described herein, such IPAAs have a boiling point near that of DVB and that can also suppress insoluble polymer formation through active functional groups thereof. As crude styrene contains DVB, a potent cross-linking agent, which forms insoluble polymer when present during styrene polymerization, the herein-disclosed IPAAs can be utilized to minimize the amount of insoluble polymer (i.e., polystyrene) formed during the production of styrene (e.g., during the purification of styrene monomer from a crude styrene stream). The IPAAs comprise one or more active functional groups comprising reactive organic species with oxygen, hydrogen, nitrogen and/or similar active sites. Such organic species include, without limitation, alcohols, aldehydes, ketones, acids, and labile hydrogen. Insoluble polymer fouling can reduce production, shorten run lengths and lengthen turnarounds. Thus, the IPAAs, IPACs, compositions, systems and methods of this disclosure may provide for increased production, longer run lengths, and/or shortened turnaround times, in embodiments.

At least two such IPAAs can be prepared from styrene by aerobic oxidation. Utilization of a portion of the tar stream (and/or another stream, such as, without limitation, styrene product 127/227/327) from the styrene purification section to produce the IPAA(s) enables the production of the IPAA(s) on-site, thus reducing cost of the fouling reduction. For example, production of acetophenone and benzaldehyde from a portion of the tar stream from the styrene purification section via aerobic oxidation of the tar stream under mild conditions, as described herein, in the presence of an oxidation catalyst, as described herein, enables on-site production of the IPAA(s) utilized for the reduction of fouling, in embodiments. In embodiments, IPAA(s) can thus be prepared from process streams in the styrene production system or plant and injected back to the process to provide protection against insoluble polymer fouling.

The costs of insoluble polymer fouling can be high as both production losses and maintenance expenditures can be incurred. The IPAAs, IPACs, systems, and methods disclosed herein can reduce such costs.

EXAMPLES

Example 1: Additive Performance for Insoluble Polymer Abatement

The ability of various additives to control insoluble polymer formation was tested. Performance evaluations were conducted in liquid phase using a 6-port test system. A common heating block with six ports that can hold 25(D)×150(H) mm test tubes was utilized, thus allowing the simultaneous operation of six separate solutions. Each tube was sealed with a septum cap, and a common nitrogen header was used to purge each tube. Nitrogen purge was introduced into the test tubes using 1/16" tubing extending through the septum cap. A syringe needle was used to vent purge gas.

Test solutions containing about 60 weight percent (wt %) styrene were collected as crude styrene samples from lab adiabatic pilot units. The crude styrene was spiked with DVB to produce 0.1% (wt) concentration. The additives were used in the same concentration, 0.1% (wt). Crude styrene with 0.1% (wt) DVB was used as the reference sample. For the evaluation, 10 g of a solution was placed in a test tube and purged with nitrogen at room temperature. The heating block was set at 120° C. and allowed to stabilize before introducing the test solutions. After purging each solution, each test tube was moved into the heating block ports. Samples were taken after 15 and 30 minutes. Each sample was analyzed by gas chromatography (GC) using a method that can measure low levels of DVB and quantitatively analyze the usual crude styrene species, including benzene, toluene, EB, styrene, DVB, ethyl-vinyl benzene and phenylacetylene. The test solutions were also tested gravimetrically for polymer and heavies using a solids analyzer comprising an electronic balance with a high intensity infrared lamp operable to evaporate monomer. The change in the DVB concentration (a decrease of which can correlate with insoluble polymer formation) and the soluble polymer formation were recorded.

The additives tested in this Example are listed in Table 1. Species to be tested were chosen based on their boiling points, having boiling points higher than that of styrene and close to that of DVB. The boiling points of the additives tested are also shown in Table 1; styrene and DVB and their boiling points are included for reference.

TABLE 1

Selected Additives and Boiling Points Thereof for Screening Study at 120° C. using Crude Styrene

| Additive or Component | BP (° C.) |
|---|---|
| N,N-DiEt PDA | 268 |
| Biphenyl | 254 |
| Di-propylene glycol | 233 |
| Terpineol | 215 |
| Ethyl Benzoate | 212 |
| Tetralin | 207 |
| Acetophenone | 202 |
| Methyl Benzoate | 198 |
| DVB | 195 |
| Propylene Glycol | 189 |
| Ethyl Carbamate | 183 |
| Ethyl Acetoacetate | 181 |
| DPGME | 180 |
| Benzaldehyde | 178 |
| Styrene | 145 |

The results for 1000 ppm of each additive after 30 minutes at 120° C. in crude styrene dosed with 1000 ppm of DVB are shown in FIG. 3, which is a bar graph of % DVB change and percent polymer growth for the additives of Example 1. (In FIG. 3, Bzald is benzaldehyde, PhE is 1-phenylethanol, BZDMA is benzaldehyde dimethyl acetal, DPC is diphenyl carbonate, ET Lactate is ethyl lactate, Etaceto acetate is ethylaceto acetate, AcPhen is acetophenone, dpgme is dipropylene glycol methyl ether, DiET-amino-EtOH is diethyl-amino ethanol, DiPG is dipropylene glycol, PG is propylene glycol, and N,N-diEt PDA is N,N-dethyl-1,4-phenylenediamine.)

Additives tested included N,N-diethylphenylenediamine, methyl carbamate, ethyl carbamate, methyl benzoate, ethyl benzoate, di-propylene glycol, diethylamino-ethanol, biphenyl, cyclohexanol, and ethylaceto-acetate; the functional groups of the active species tested included amines, amino-alcohols, labile C—C bonds, esters, and carbamates. Amines, glycols, benzoates and carbamates produced notably good results.

Most additives evaluated showed correlation of their % PS formation and the % DVB change, suggesting they function by inhibiting the initiation and/or the propagation of styrene polymerization. This may be expected, as DVB is consumed by free radical polymerization; once polymerization takes place, DVB will be incorporated into the polymer. However, as discussed below, there were some exceptions to this correlation. The results of all additives in the trial are compiled in FIG. 4, which is a plot of percent soluble polystyrene (PS) polymer formation as a function of percent DVB change for the additives of Example 1.

Without wishing to be limited by theory, it is believed that benzaldehyde reacted with DVB to show a high consumption of DVB during the course of the test. Benzaldehyde also inhibited the formation of polymer. The two benzoate species also did not align with the correlation of the other species. Both the methyl benzoate and the ethyl benzoate showed small changes in % DVB. Ethyl benzoate showed no ability to inhibit polymer formation, while methyl benzoate showed moderate inhibiting performance. Again, without wishing to be limited by theory, this suggests some other interaction with DVB that prevents its incorporation into radical polymerization and cross-linking of polymer, and also suggests that benzoate derivatives may be mixed with standard anti-polymerization inhibitors to prevent DVB cross-linking by selectively suppressing its reaction.

Example 2: Crude Styrene Condensate Area Fouling Study

As noted hereinabove, a first major area of a styrene production plant for potential issues with insoluble polymer fouling/formation is the heat exchanger area where condensation of the gas phase reactor effluent is cooled and liquefied. This condensate area has sufficient temperature to initiate styrene polymerization, and the concentration of DVB can be sufficient to form insoluble polymer. DVB has a higher boiling point of 195° C. and liquefies before styrene during condensation; DVB can also thermally initiate polymerization. Accordingly, a testing apparatus was designed to mimic conditions where gas phase crude styrene and steam are condensed into liquids.

Figure 5:
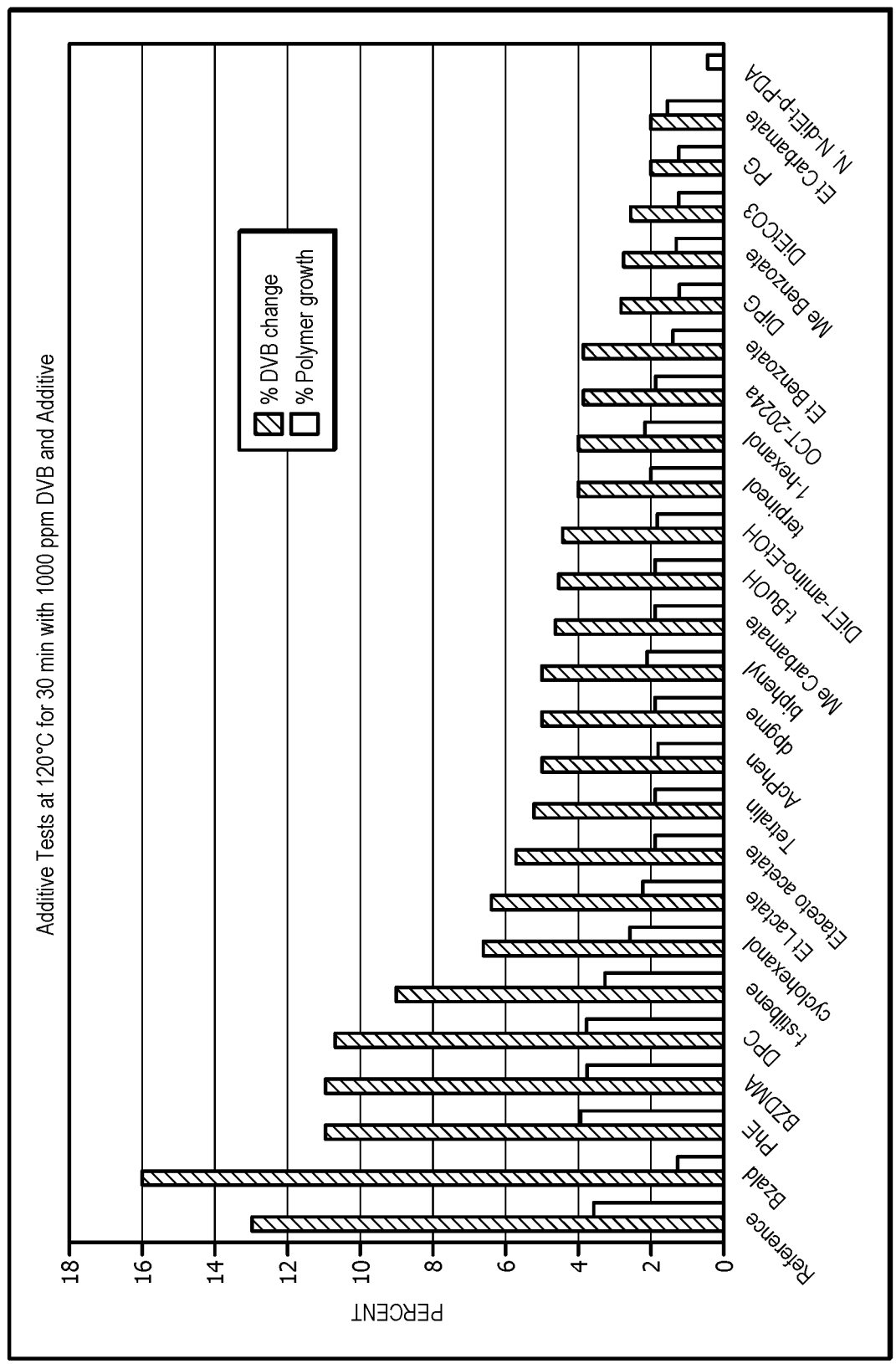
FIG. 5 is a bar graph of percent (%) DVB change and percent soluble polymer growth in batch testing of the additives of Example 1 and selected reference species.

A crude styrene feed was prepared from EB dehydrogenation lab reactor effluent comprising about 55-65 wt. % styrene, 35-45 wt. % EB, 2 wt. % benzene/toluene, and trace by-products to which an additional 500 ppm of DVB was added. FIG. 5 is a schematic diagram of the crude styrene condensate test apparatus 300 of Example 2. ISCO syringe pumps 301 and 302 were used to add the crude styrene and water for steam creation, respectively, into the system. The main vessel 309 consisted of a horizontal tube 310, having dimensions of ½" inside diameter (ID) by 15" length, that was wrapped in heat tape 311 powered from an independent controller 312 set at 130° C. The water was fed via ⅛" tubing 304 to a pre-heat vaporization zone 306 controlled by independent controller 307 set at 135° C. to heat tape 305 connected to inlet 308 of the horizontal tube 310. The crude styrene was added via ⅛" tubing 303 with the steam at the inlet 308 of the horizontal tube 310. The effluent 313 passed through a water-cooled condenser (not shown) and into a sample collection or effluent bottle 314. Nitrogen was introduced via 90 PSI nitrogen utility line and regulator 315 and tubing 316 to purge horizontal tube 310 between experiments. The nitrogen was used remove oxygen before experiments and to clear the apparatus between experiments.

Individual experiments were conducted by adding selected additives to the crude styrene. Dosages listed are based on the hydrocarbon portion only, excluding the steam/water. Heat tapes 305 and 311 were started first and allowed to reach their set points (i.e., 135° C. and 130° C., respectively). The water pump was started at 0.25 mL/min and run until the system stabilized with only steam. The crude styrene pump was then started at 0.5 mL/min. Tubing 310 of main vessel 309 maintained a temperature in the range of 110° C. to 140° C. Most experiments were conducted at 110° C. or 130° C. The data from the 130° C. experiments was used to select the acceptable additives. After four hours, a composite effluent sample was collected and analyzed by GC along with a crude styrene feed sample. The change in DVB (weight percent loss by GC) in concentration from the feed to the effluent was reported; the greater the loss of DVB, the more insoluble polymer is presumed formed. The formation of insoluble polymer was confirmed by inspection of the horizontal tube after experiments were conducted.

Figure 6:
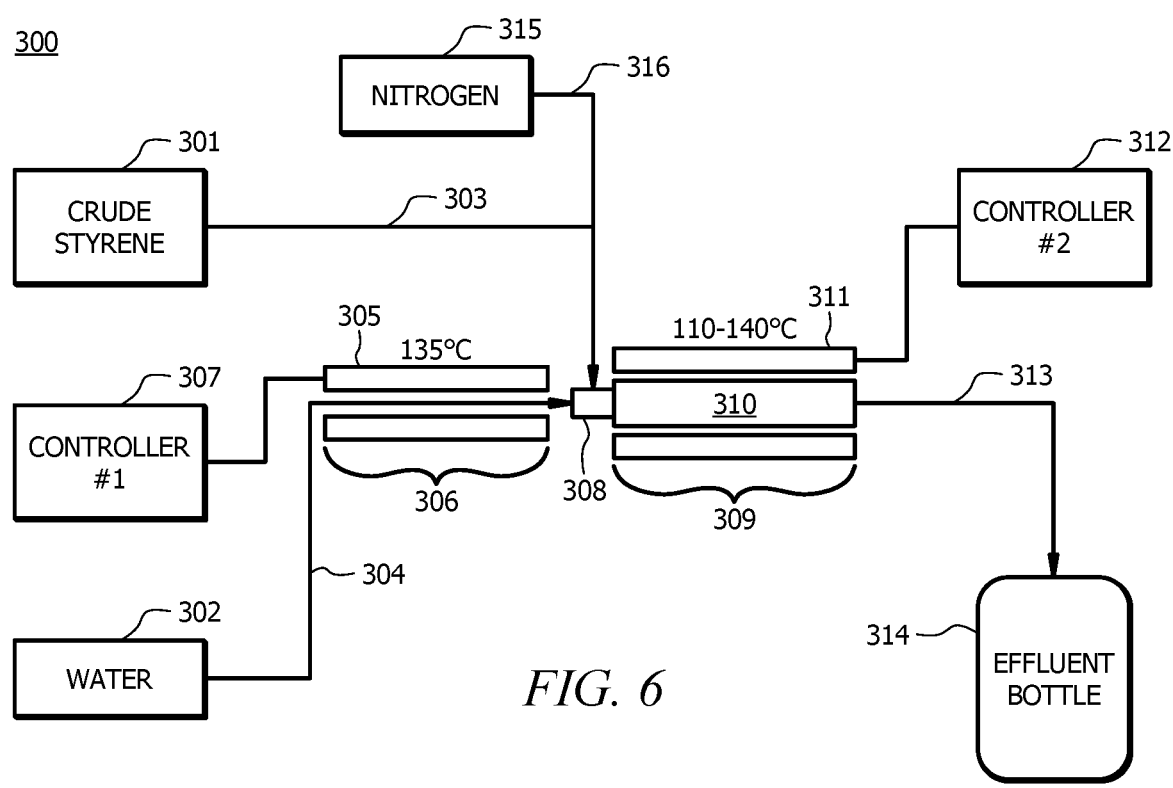
FIG. 6 is a schematic diagram of the crude styrene condensate test apparatus of Example 2.
Figure 7:
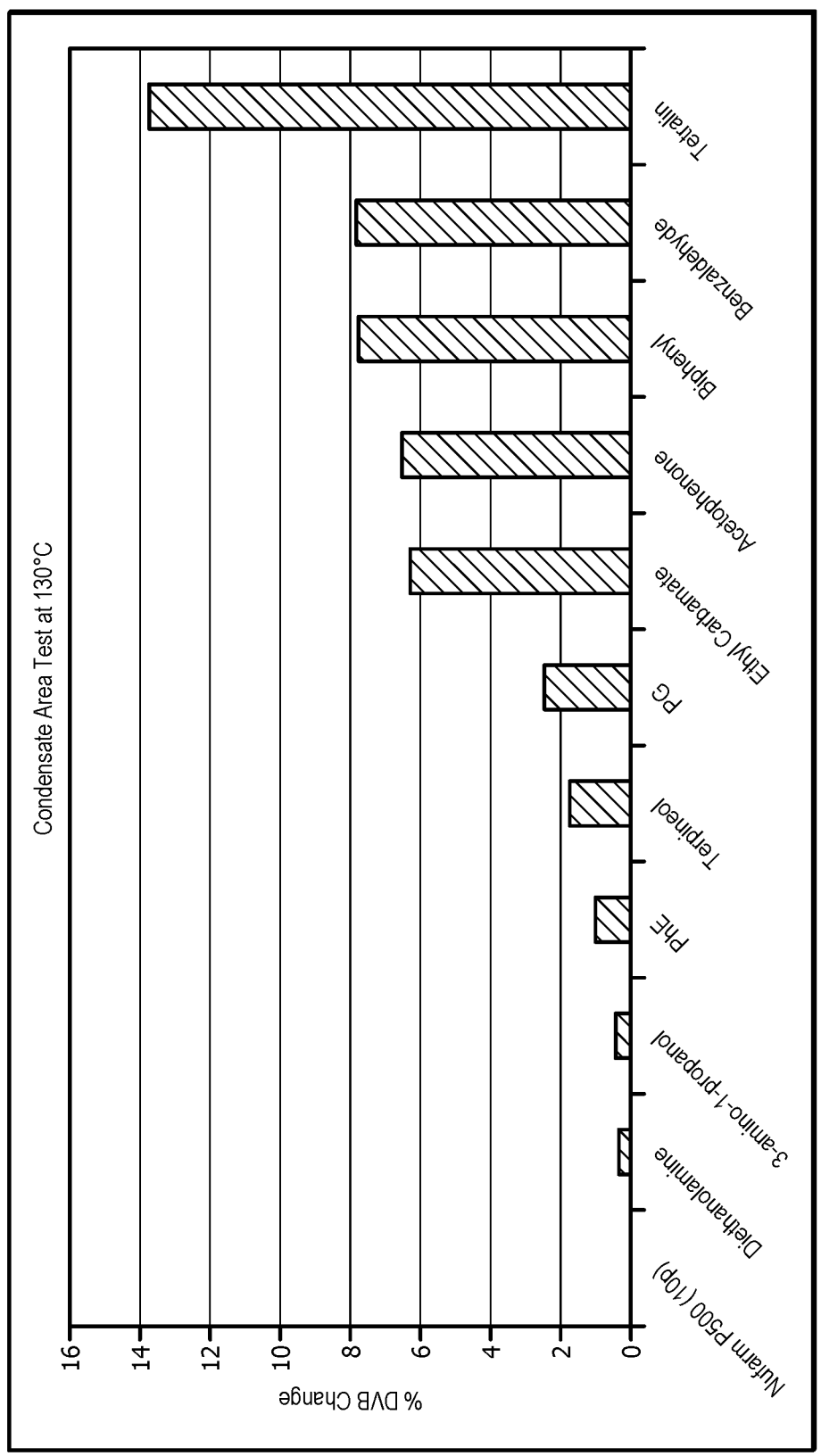
FIG. 7 is a bar graph of the percent (%) DVB change for the condensate testing results of Example 2.

Several candidates with appropriate physical properties were evaluated via the crude styrene condensate test apparatus described above, and the condensate additive testing data obtained are shown Table 2 below and in FIG. 6, which is a bar graph of the percent DVB change for the condensate testing results of Example 2.

The additives were tested at 200 ppm dosages. PhE (phenylethanol), terpineol and PG (propylene glycol) showed high performance while ethyl carbamate, acetophenone, biphenyl and benzaldehyde produced intermediate performance. Tetralin had low activity in this first testing area (A1), and is included mainly for comparison.

TABLE 2

Results from Example 2

| Additive | PPM | Tube T (° C.) | WT. % DVB Change |
|---|---|---|---|
| diethanolamine | 200 | 130 | 0.26 |
| 3-amino-1-propanol | 200 | 130 | 0.40 |
| 1-Phenylethanol (PhE) | 200 | 130 | 1 |
| Terpineol | 200 | 130 | 1.7 |
| Propylene Glycol (PG) | 200 | 130 | 2.4 |
| Ethyl Carbamate | 200 | 130 | 6.2 |
| Acetophenone | 200 | 130 | 6.4 |
| Biphenyl | 200 | 130 | 7.6 |
| Benzaldehyde | 200 | 130 | 7.7 |
| Tetralin | 200 | 130 | 13.5 |

This Example studied the performance of additives for the condensate region of a styrene production plant at the point where high-temperature, gaseous reactor effluent is converted to liquid. At this ('first area') location, steam is present and a steep temperature gradient is found. The suspected primary cause of the fouling seen in this area is the higher boiling point of DVB that could result in hot, liquid DVB condensing before styrene/EB, and thus initiating insoluble polymer formation. Commercial inhibitors have a very high boiling point and would condense before DVB but many may have thermal instabilities if higher temperatures, such as those encountered here, are present. Also such commercial products could be expensive for use in this application. A readily-available, inexpensive compound with chemical activity and a boiling point near that of DVB, such as the additives of this disclosure, provide an attractive option for solving this problem.

Example 3: Oxidation Catalysts for Styrene to Benzaldehyde and Acetophenone Using Styrene Plant Streams at Mild Conditions As a catalyst to drive the production of benzaldehyde and acetophenone to target levels (e.g., 1-2 wt %) at relatively mild conditions from styrene plant process streams, oxygen-activating species on a robust support were studied. Known oxygen activation metals and two alumina supports were investigated in this Example 3.

Oxidation catalysts were prepared by the standard incipient wetness method. Two supports purchased from Alfa Aesar were used: an intermediate surface area alumina extrudate (Al1) and a macroporous, low surface area silica-alumina sphere (Al4). The Al1 support (Alfa-43857) is a ⅛" (3.1 mm) alumina extrudate catalyst support with low silica content, a liquid pore volume of 0.44-0.54 mL/g, and a surface area in the range of 80-120 m/g. The Al4 support (Alfa-43863) is a 3/16" (4.5 mm) alumina sphere comprising 13% silica, an average pore diameter of 75 microns, a surface area of less than or equal to about 0.1 m$^2$/g, and a liquid pore volume of 0.21 mL/g.

The active phases chosen for this Example 3 (Co, Mn, Fe and Mo) are oxygen activating species. The starting materials used were cobalt (III) nitrate hexahydrate, manganese (II) nitrate-50 wt % aqueous solution, iron (III) nitrate nonahydrate, and ammonium heptamolybdate tetrahydrate. After adding the starting materials from aqueous solutions, the catalysts were dried at 150° C. then calcined in air for 1 hour sequentially at 200, 300 and 400° C. The quantities are shown in Table 3. After calcination, the cobalt and manganese catalysts were black/gray colored, the iron catalyst was brown and the molybdenum catalyst light slate-gray. Another commercial catalyst comprising a 0.3 wt % Pd on 1.8" (3.1 mm) alumina spheres was also evaluated. This commercial catalyst was obtained from a hydrogenation reactor and was been regenerated prior to use.

TABLE 3

Compilation of the Oxidation Catalyst Preparation Details of Example 3

| Catalyst | support grams | active material | active mat grams | active mat g/mol | active mat moles | calcined formula | g/mol | active phase stoich | active phase grams | active phase wt % |
|---|---|---|---|---|---|---|---|---|---|---|
| Co2-Al1 | 90 | Co(NO3)3-6aq | 5.4 | 291 | 0.018557 | Co2O3 | 165.8 | 2 | 1.54 | 1.68 |
| Co4-Al1 | 102.45 | Co(NO3)3-6aq | 1.84 | 291 | 0.006323 | Co2O3 | 165.8 | 2 | 0.52 | 0.51 |
| Co3-Al4 | 99 | Co(NO3)3-6aq | 1.76 | 291 | 0.006048 | Co2O3 | 165.8 | 2 | 0.50 | 0.50 |
| repeat | 173.35 | Co(NO3)3-6aq | 3.07 | 291 | 0.01055 | Co2O3 | 165.8 | 2 | 0.87 | 0.50 |
| repeat | 171 | Co(NO3)3-6aq | 3.03 | 291 | 0.010412 | Co2O3 | 165.8 | 2 | 0.86 | 0.50 |
| repeat | 186.6 | Co(NO3)3-6aq | 3.31 | 291 | 0.011375 | Co2O3 | 165.8 | 2 | 0.94 | 0.50 |

TABLE 3-continued

Compilation of the Oxidation Catalyst Preparation Details of Example 3

| Catalyst | support grams | active material | active mat grams | active mat g/mol | active mat moles | calcined formula | active phase g/mol | active phase stoich | active phase grams | active phase wt % |
|---|---|---|---|---|---|---|---|---|---|---|
| Mn-Al1 | 74.2 | Mn(NO3)2 (50% sol) | 6 | 357.8 | 0.016769 | MnO2 | 86 | 1 | 1.442 | 1.91 |
| Mn2-Al4 | 99 | Mn(NO3)2 (50% sol) | 4 | 357.8 | 0.011179 | MnO2 | 86 | 1 | 0.961 | 0.96 |
| Fe-Al4 | 100 | Fe(NO3)3-9aq | 2.56 | 404 | 0.006337 | Fe2O3 | 159.7 | 2 | 0.50598 | 0.50 |
| Mo-Al4 | 100 | Amm Heptamolybdate | 4.62 | 1235.86 | 0.026168 | MoO3 | 143.9 | 1 | 3.77 | 3.63 |

Figure 8:
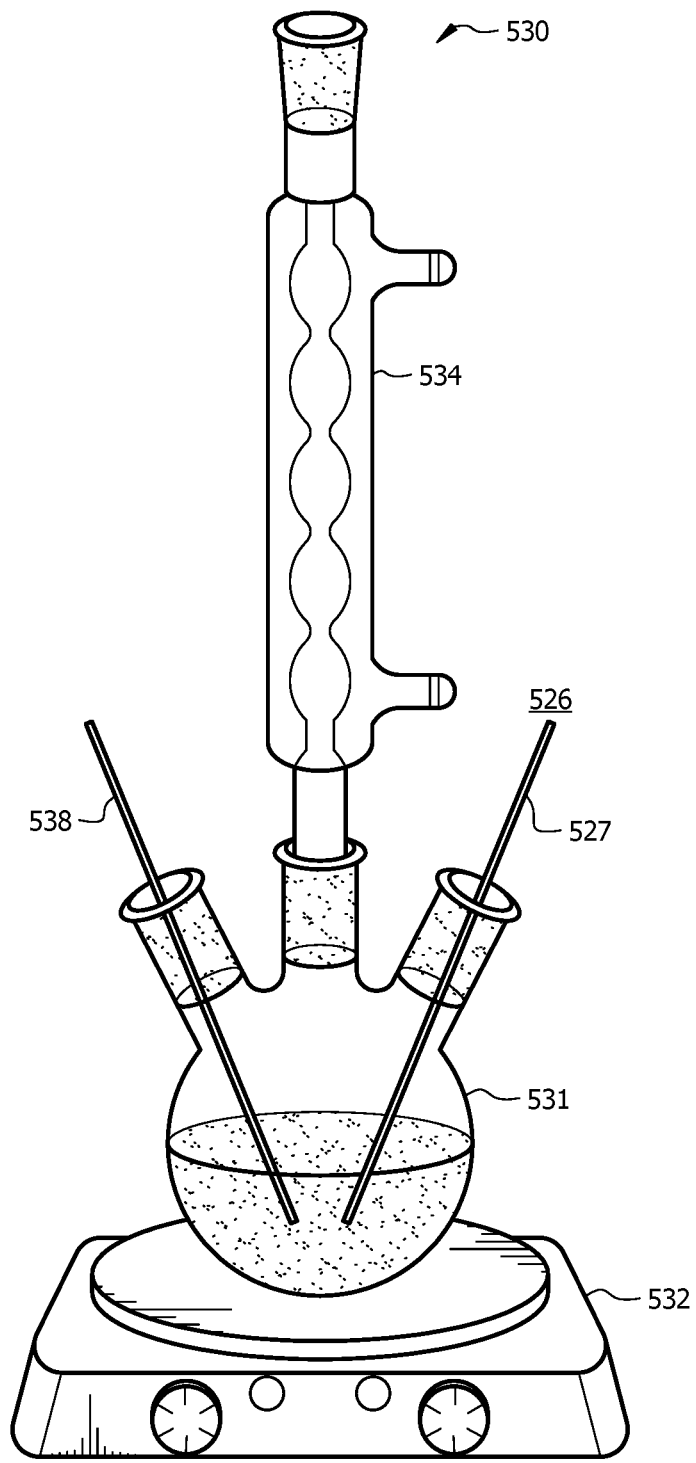
FIG. 8 is a schematic of a batch reactor of Example 3 utilized for the evaluation of oxidation catalysts for the production of oxidation products including benzaldehyde and acetophenone from styrene plant streams.

The catalytic results were conducted using batch tests. As described with reference now to FIG. 8, which is a schematic of a batch oxidation system 530 utilized for the evaluation of the oxidation catalysts of this Example 3 for the production of oxidation products including the IPAAs benzaldehyde and acetophenone from styrene plant streams. A 250 mL three-neck round bottom flask 531 was used with a heating mantle 532 and TC 533. TC 533 was connected to a controller (not depicted in FIG. 8). The 24/40 joints on flask 531 were capped with septa. The air 526 was introduced at the bottom of the flask via a ⅛" (3.1 mm) tube 527 and controlled by a rotameter. All tests were conducted using the same batch of crude styrene from a styrene production system, which was a sample of a first styrene finishing column bottoms comprising 95.5% styrene monomer (SM). The styrene feed (e.g., 129, 229, 329) was used as received. The crude styrene (125 mL) was added to the flask followed by 10 grams of catalyst. A water-cooled condenser 534 was placed at the top of the flask 531. The air flow was set and the heating started; time zero was counted as when the liquid temperature reached the set point of 120° C. (some experiments were conducted at 110° C.). Samples were taken at 60 and 180 minutes during each run. Samples were analyzed by GC using a standard complete-analysis styrene method. The percent benzaldehyde and acetophenone (% B&A) were summed and reported as "% B&A".

The data set for the comparison of the different catalysts of this Example 3 is shown in Table 4. The tests were conducted using 10 g of catalyst at 120° C. with 30 mL/min air addition. The data is from the 180 minute samples and shows the % B&A for each.

TABLE 4

Percent B&A Produced via Oxidation Catalysts of Example 3

| Catalyst | % B&A at 180 minutes |
|---|---|
| Co3—Al4 | 1.4 |
| Mn2—Al4 | 1.3 |
| Mo—Al4 | 0.9 |
| Fe1—Al4 | 0.7 |
| Al4 (Support Only) | 0.7 |
| Co2—Al1 | 0.5 |
| Mn—Al1 | 0.3 |
| Pd/Al$_2$O$_3$ | 0.2 |

The effects of temperature and air flow rates were also investigated in this Example 3. The Co3-Al4 catalyst was evaluated at different conditions. The temperature was lowered to 110° C. and the % B&A at 180 minutes dropped to 0.8%. At temperatures higher than 120° C., significant polymer formation was observed, making the data less reliable at such elevated temperatures. The air flow was increased (50 mL/min) at 120° C. for Co3-Al4 and the % B&A increased to 1.6% B&A. Thus, temperature greater than or equal to 120° C. and a higher air flow rate appear to favor the % B&A produced.

Figure 9:
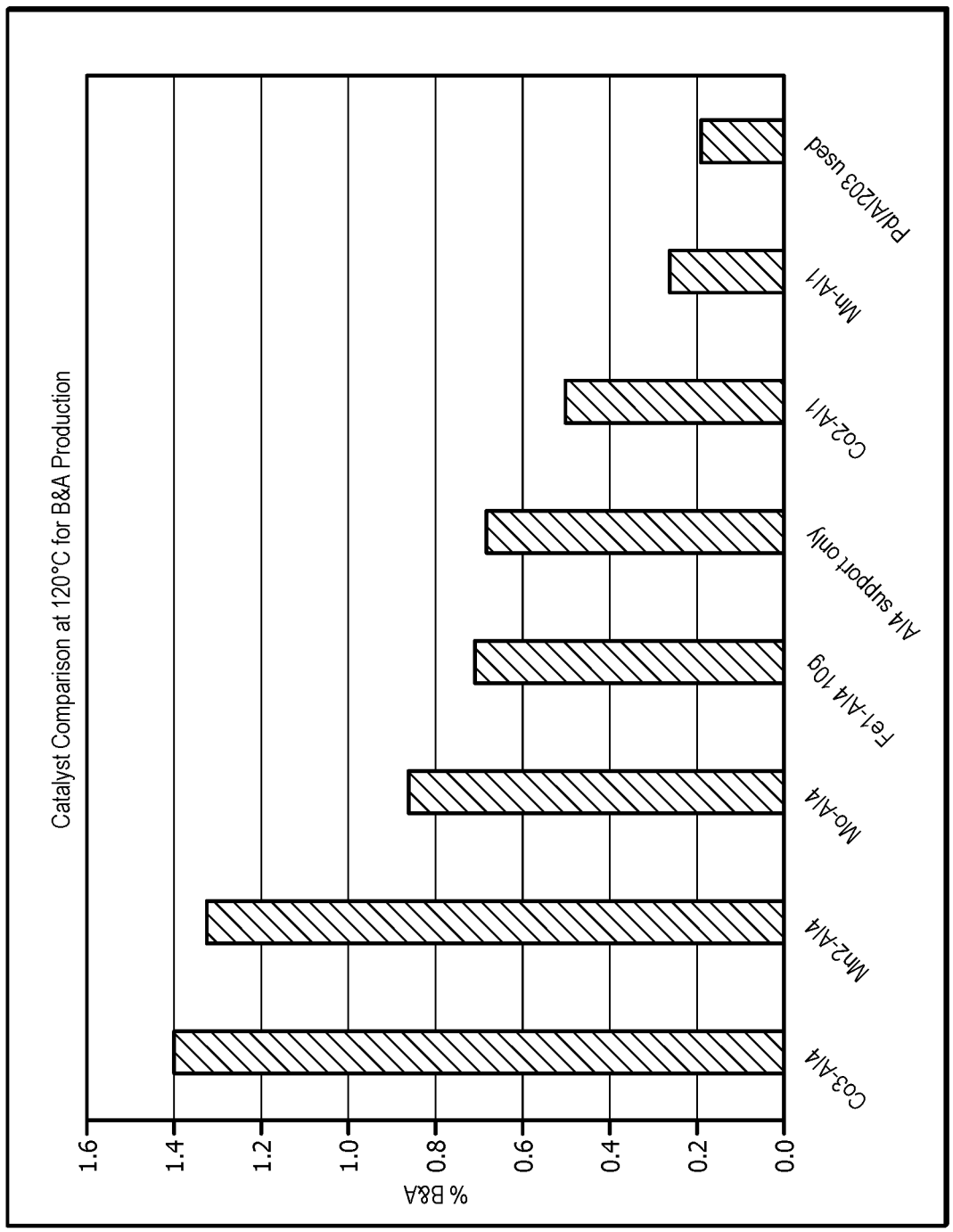
FIG. 9 is a plot of the percent benzaldehyde and acetophenone (% B&A) for the oxidation catalysts of Example 3.

At higher production rates, approximately equal amounts of benzaldehyde and acetophenone were produced. At lower production, two to three times more benzaldehyde was formed than acetophenone. FIG. 9 is a plot of the % B&A for the oxidation catalysts of this Example 3. FIG. 9 shows the performance ranking of the tested oxidation catalysts, with better increasing performance to the left of FIG. 9.

The Co—Al4 exhibited the best performance, and the Mn—Al4 exhibited the second best performance. If the dosage of B&A needed for insoluble polymer abatement is estimated to be provided by a target production of 1-2 wt % B&A, both the Co and Mn oxidation catalysts of this Example 3 have the capability to produce this total IPAA amount of benzaldehyde and acetophenone.

Example 4: Reactor Performance for the Aerobic Oxidation of Styrene Tar to Insoluble Polymer Abatement Additives As noted herein, two species identified as insoluble polymer abatement additives (IPAA) that can be prepared by oxidation of styrene are benzaldehyde and acetophenone (B&A). Utilizing such compounds as IPAAs can allow for the preparation of the IPAAs directly from styrene process streams. This Example 4 describes the oxidation catalyst performance for a process using styrene tar streams as the feedstock for mild aerobic oxidation for the (e.g., onsite) production B&A in sufficient quantities for implementation in a styrene production system.

A continuous flow reactor system was constructed to study catalyst performance for the oxidation of styrene tar streams to produce benzaldehyde and acetophenone (B&A). Styrene tar in this Example 4 comprised a bottoms stream from a first styrene finishing column (such as fourth column D4 of the embodiment of FIG. 2 or third distillation column D3 of the embodiment of FIG. 3). The styrene tar contained roughly 92-96% styrene. Actual plant samples were used and thus contained polymerization inhibitors, polymer, and other heavy species in addition to the styrene. Oxidation catalysts (as described in Example 3 hereinabove) tested in this Example 4 comprised cobalt or manganese.

Figure 4:
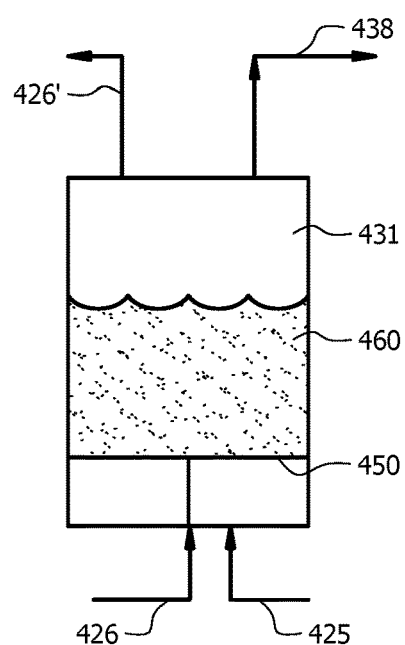
FIG. 4 is a schematic of an oxidation system IV according to an embodiment of this disclosure.

The reaction was run in up flow for both the styrene tar feed (e.g., the styrene-containing stream in styrene-containing stream line 425 of FIG. 4) and air (e.g., air stream in air inlet line 426 of FIG. 4). The oxidation reactor (e.g., oxidation reactor 431 of FIG. 4) comprised a reactor vessel prepared from a 150 mL stainless steel vessel (5" L by 2" D) with a bored through tee-fitting to allow the simultaneous introduction of styrene tar (e.g., in styrene-containing stream line 425) and air (in air inlet line 426) at the bottom of the oxidation reactor. Another bored-through tee-fitting was located at the top of the reactor for the internal control TC and to disengage the liquid effluent from the excess air (e.g., in excess air line 426' in FIG. 4). The liquid was collected in a sample bottle while the excess air passed through a knock-out pot to the vent line. The reactor was heated with a silicone-coated heating tape using an internal TC and controller. In this Example 4, the liquid styrene tar feed was introduced by an ISCO 500 C syringe pump and the air flow was controlled using a rotameter and metering valve. The liquid feed was actual plant sampled from the bottoms product of the styrene purification column and it was used as received. Samples were collected hourly; the 5 hour sample was used for the final results to allow sufficient time for equilibration. Repeat runs were made at each condition and were averaged. Multiple catalyst batches were made and tested. Both the cobalt and manganese catalysts, described in Example 3, showed no deactivation after weeks of use. The data shown in Table 5 were collected using the same catalyst batch and styrene tar batch for all the runs.

TABLE 5

Performance Data for Styrene Tar Oxidation of Example 4

| | | % B&A at 5 hours | |
|---|---|---|---|
| Tar Flow (mL/min) | Air Flow (cc/min) | Co—Al4 | Mn—Al4 |
| 1 | 100 | 1.1 | 1 |
| 1 | 80 | 0.9 | 1.1 |
| 1 | 50 | 0.7 | 0.7 |
| 0.8 | 100 | 1.8 | 1.2 |
| 0.8 | 80 | 1.3 | 1.4 |
| 0.8 | 50 | 1 | 1 |
| 0.6 | 100 | 2.3 | 2 |
| 0.6 | 80 | 1.8 | 2 |
| 0.6 | 50 | 1.4 | 1.2 |

In this Example 4, the production of insoluble polymer abatement additives, IPAA, from styrene streams in the distillation columns of styrene plants was being investigated using laboratory reactor systems. Benzaldehyde and acetophenone were prepared by mild aerobic oxidation of styrene. As noted above, these two species have shown activity in insoluble polymer abatement in mixtures of styrene and DVB. As detailed above, the production of B&A from on-site styrene streams can enable production of these additives with subsequent re-introduction into the purification system 120/220/320 for insoluble polymer abatement. In embodiments, only 1-2% B&A production (or less) from a plant stream may be needed to produce sufficient IPAA for use as IPAA in the styrene production plant. Accordingly, the tests of this Example 4 were performed to study the formation of B&A from plant styrene streams.

In this Example 4, a laboratory reactor system was used to investigate reaction conditions on the production of benzaldehyde and acetophenone (B&A). A portion of a bottoms stream from the first styrene purification column was utilized as the styrene-containing feedstock to the oxidation reactor in this Example 4. This feed stock comprised a high styrene content, high polymerization inhibitor levels and substantially no EB that could potentially compete for oxidation. An oxygen-activating catalyst as described in Example 3 hereinabove was utilized to keep the temperature below the practical threshold for liquid styrene use (i.e., to prevent styrene self-initiation). An oxidation reaction temperature of 120° C., which was found to be optimal, was utilized in this Example 4.

Figure 10:
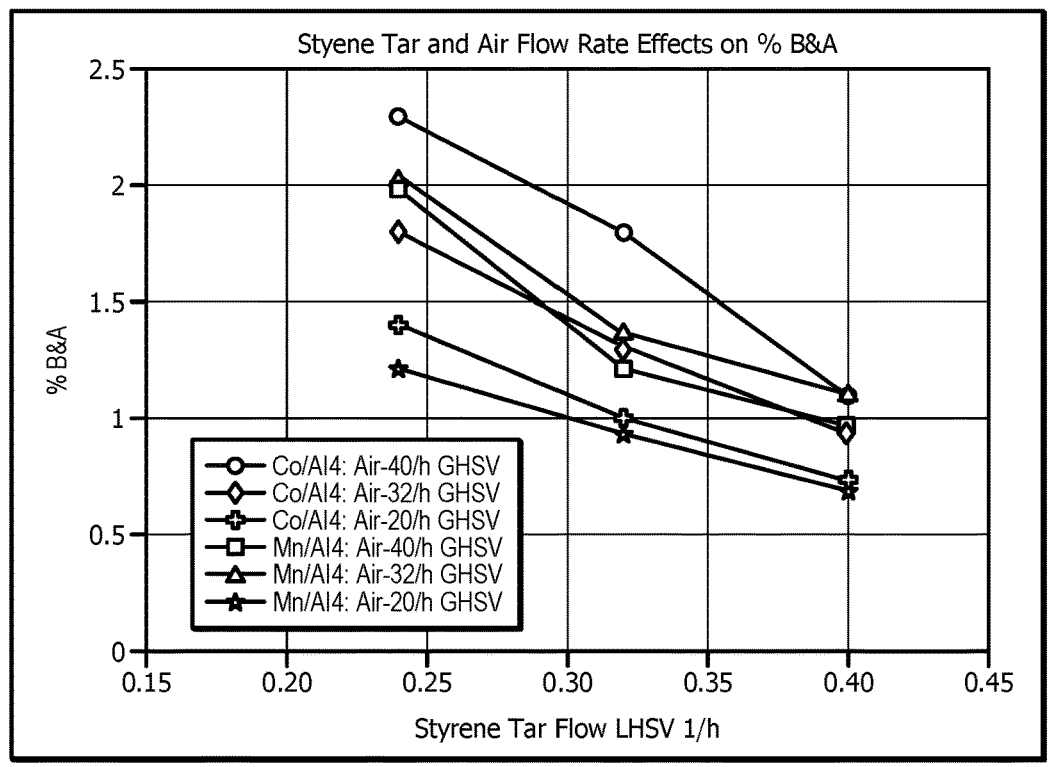
FIG. 10 is a plot of the percent benzaldehyde and acetophenone (% B&A) produced with the oxidation catalysts of Example 4 at selected tar and air flow rates at 120° C.

An up-flow tubular catalytic reactor was used. A cobalt catalyst (as described in Example 3) having a low surface area and comprising a macroporous support and a manganese analog (also described in Example 3) that showed nearly identical performance were utilized in this Example 4. Several different levels of styrene tar flow and air flow were studied in this Example 4. The results for three liquid hourly space velocity (LHSV) levels for styrene tar and three gas hourly space velocity (GHSV) levels for air at 120° C. are shown in FIG. 10, which is a plot of the percent benzaldehyde and acetophenone (% B&A) produced with the oxidation catalysts of this Example 4 at the selected tar and air flow rates at 120° C. The data depicted in FIG. 10 was acquired from the 150 mL catalyst bed. The styrene tar flows of 1, 0.8 and 0.6 mL/min that were examined correlate to space velocities of 0.4, 0.32 and 0.24 h$^{-1}$ LHSV. The air flows of 100, 80 and 50 cc/min that were examined correlate to 40, 32 and 20 h$^{-1}$ GHSV.

In FIG. 10, the production B&A (wt % B&A) is plotted versus the styrene tar flow rate. Separate curves (delineated in the inset box) show the effect of air flow rate. Results for both cobalt and manganese oxidation catalysts of this disclosure are presented in FIG. 10. The projected conversion levels (1-2 wt %) of B&A needed for manufacturing implementation were demonstrated at most conditions. As can be seen in FIG. 10, higher styrene tar flow rates resulted in lower B&A production, while, conversely, higher air flow rates resulted in higher B&A production. The cobalt catalyst exhibited slightly better performance than the manganese analog in this Example 4.

Figure 11:
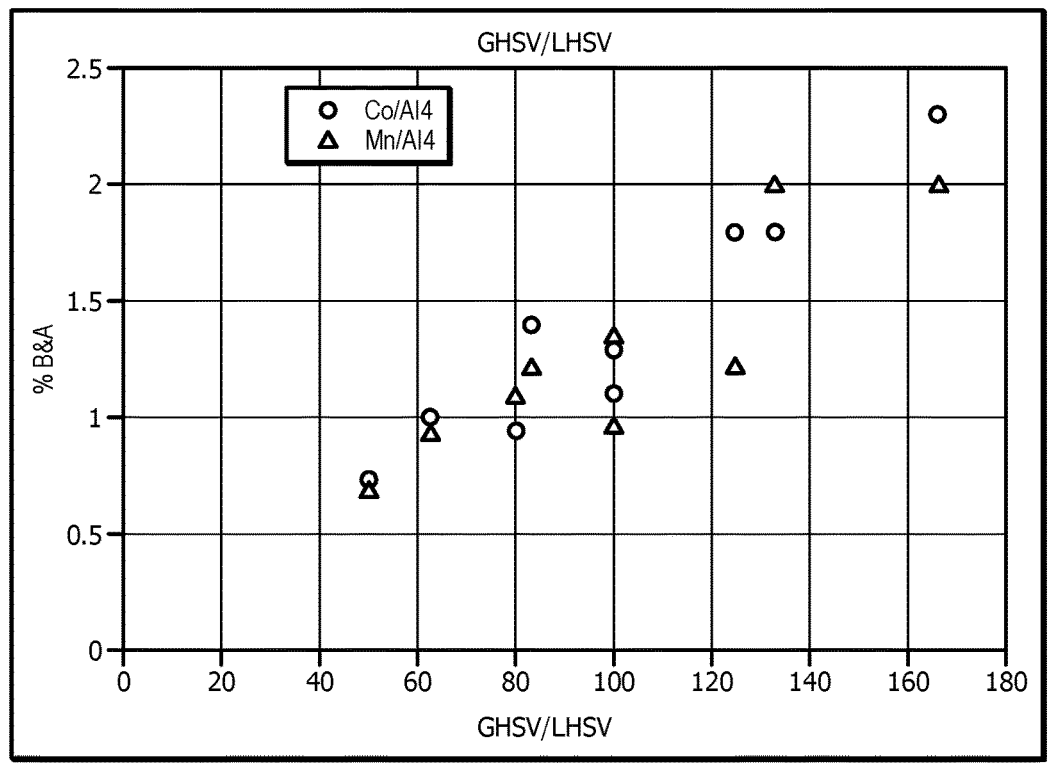
FIG. 11 is a plot of the percent benzaldehyde and acetophenone (% B&A) as a function of the ratio GHSV/LHSV of the gas hourly space velocity (GHSV) of air to the liquid hourly space velocity (LHSV) of the styrene containing stream for the experiments of Example 4.

From the data of FIG. 10, the general operating guidelines for production of % B&A can include maximizing the air flow rate and minimizing the liquid styrene tar stream feed flow rate. FIG. 11 is a plot of the percent benzaldehyde and acetophenone (% B&A) as a function of the ratio GHSV/LHSV of the gas hourly space velocity (GHSV) of air to the liquid hourly space velocity (LHSV) of the styrene containing stream for the experiments of this Example 4. FIG. 11 thus shows this relationship of flow rates by correlation of the % B&A production versus the ratio of air GHSV and styrene tar LHSV. With the GHSV in the numerator and the LHSV in the denominator, the production of % B&A increases as the ratio increases. Most of the data points are above the estimated minimum production level of 1 wt % B&A. Other flow rates of air and styrene feeds are possible and within the scope of this disclosure.

This Example 4 shows that (at least) two species identified herein as IPAAs, benzaldehyde and acetophenone, can be prepared from styrene by aerobic oxidation at mild conditions. This Example 4 confirms that these additives can be prepared from styrene distillation column streams. A low temperature catalytic oxidation reactor successfully produced sufficient amounts of B&A in this Example 4 from actual plant samples. As detailed hereinabove, a process slip stream can be utilized to prepare IPAA(s) for re-injection to the front of the styrene purification section 120/220/320 (e.g., to an EB recycle column such as third distillation column D3 of FIG. 2 or second distillation column D2 of FIG. 2).

Figure 12:
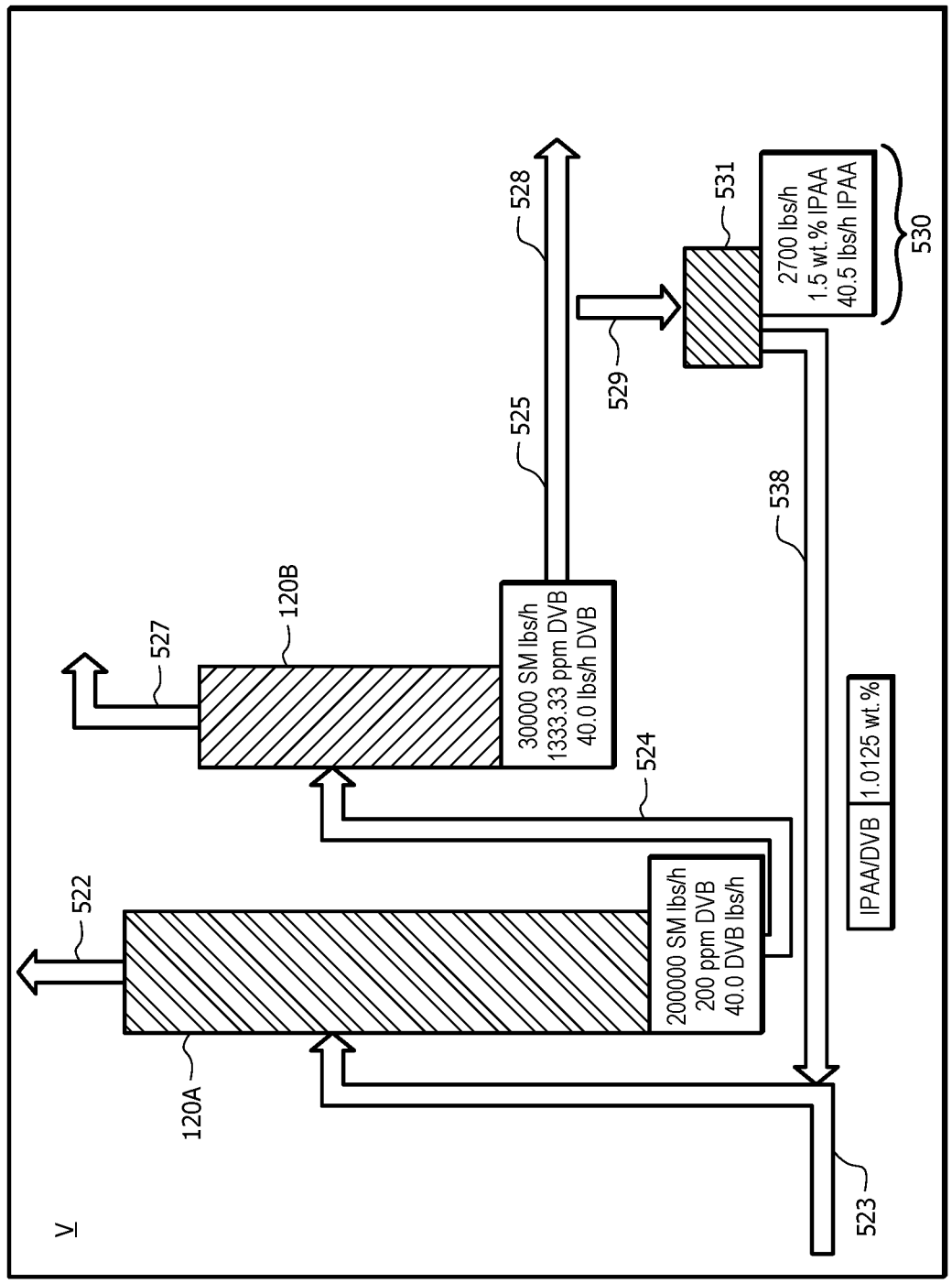
FIG. 12 is a schematic representation of an exemplary part of a styrene production system V, as described in Example 5.

Example 5: Exemplary Styrene Production System V Comprising Styrene Tar Oxidation FIG. 12 is a schematic representation of an exemplary part of a styrene production system V comprising an in situ IPAA production system (e.g., oxidation section 530), as described in this Example 5. In this example, an EB recycle or separation column 120A is configured to separate an EB stream in EB tops line 522 from an EB separation/recycle column feed in feed line 523 comprising EB, styrene monomer (SM), and heavier components (e.g., polymer, tar) and provide a bottoms stream in bottoms product line 524 comprising styrene and the heavies. The streams can further comprise anti-polymerization additives (e.g., IPAA(s) of this disclosure and/or conventional polymerization retarders, such as, without limitation, TMPO). A (e.g., first or only) styrene finishing column 120B is configured to separate, from the bottoms stream in bottoms product line 524 introduced from EB recycle/separation column 120A, a tops product comprising styrene via styrene line 527 and a bottoms product comprising styrene tar (e.g., tar comprising styrene, heavies components, and optionally the anti-polymerization additive(s)) in bottoms product line 525.

A slipstream of bottoms product 525 is introduced via oxidation feed line 529 into oxidation unit or reactor 531. The remainder of the bottoms product in bottoms product line 525 is removed via tar recycle and/or further processing line 528. In embodiments, one or more tar recycle and/or further processing lines 528 are configured to recycle tar/heavy residue back to a separations feed line (such as 113 in FIG. 1) or into any individual column within the separation or distillation apparatus of which distillation columns 120A and 120B are a part. In embodiments, the slip stream in line 529 removed from bottoms line 528 comprises less than or equal to about 1, 5, 10, 15, or 20 weight percent (wt %) of the bottoms stream in line 525 from the styrene finishing column 120B. All or a portion of the oxidation product removed from oxidation unit 531 via liquid oxidation reactor liquid effluent line 538, which comprises one or more IPAAs of this disclosure (e.g., at least benzaldehyde and/or acetophenone) can be recycled to EB separation distillation column 120A via liquid effluent line 538.

In the exemplary embodiment of FIG. 12, EB separation distillation column 120A provides a bottoms product in bottoms product line 524 comprising 200,000 pounds per hour (lb/h) of styrene monomer comprising 200 ppm DVB with respect to styrene (or 40.0 lb/h DVB), and styrene finishing column 120B provides a bottoms product in bottoms product line 525 comprising 30,000 pounds per hour styrene monomer comprising 1333.33 ppm DVB with respect to the styrene (or 40.0 pounds per hour DVB). A slip stream 529 of bottoms product line 525 comprising 9 wt % (2700 pounds) of bottoms product line 525 is oxidized in oxidation reactor 531 to produce an oxidation product comprising 1.5 wt % IPAAs or 40.5 pounds per hour of IPAAs (benzaldehyde and acetophenone), thus providing an amount of IPAAs that is 0.5 lb/h greater than the amount of DVB (40 lb/h) in EB separation/recycle column 120A and styrene finishing column 120B, providing a weight ratio of IPAA to DVB therein of 1.0125. All or a portion of the oxidation product in liquid effluent line 538 can be recycled to EB separation/recycle column 120A and/or styrene finishing column 120B (e.g., via fluid connection of liquid effluent line 538 with EB separation column feed line 523 and/or bottoms product line 524, for example). This Example 5 shows that 1-2 wt % production of benzaldehyde and acetophenone (combined) IPAAs from a styrene finishing column bottoms in an oxidation reactor operated at mild conditions, as described herein, can be produced. Accordingly, a slip stream (e.g., oxidation feed stream in oxidation feed line 129/229/329) of 2000-4000 lb/h can be utilized to produce a sufficient total amount of IPAAs to inhibit insoluble polymer formation in EB recycle distillation column 120A and styrene finishing distillation column 120B of this Example 5.

In this Example 5, less than 10 wt % of the styrene finishing bottoms product stream 525 is needed to make the targeted dosage of IPAA using oxidation reactor productivity levels demonstrated in Example 3. In this embodiment, the oxidation reactor liquid effluent 538 comprising the IPAAs is recycled back to the EB recycle column 120A to match the concentration of DVB therein.

Additional Description

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

The following are nonlimiting, specific embodiments in accordance with the present disclosure:

Embodiment A: An oxidation catalyst for the oxidation of styrene to benzaldehyde and acetophenone, the oxidation catalyst comprising: a porous support; and an active phase comprising an oxygen activation metal comprising cobalt (Co), manganese (Mn), iron (Fe), molybdenum (Mo), or a combination thereof.

Embodiment B: The oxidation catalyst of Embodiment A, comprising from about 0.2 to about 4, from about 0.5 to about 3.5, or from about 0.5 to about 2 weight percent (wt %) of the active phase as appropriate oxide phase and on the total weight of the oxidation catalyst after calcining.

Embodiment C: The oxidation catalyst of Embodiment A or Embodiment B, wherein the support is a low surface area support having a Brunauer Emmett and Teller (BET) surface area, determined by ASTM D3663, that is less than or equal to 20, 10, or 1 $m^2/g$.

Embodiment D: The oxidation catalyst of any of Embodiment A to Embodiment C, wherein the support comprises alumina, alumina-silica, or a combination thereof.

Embodiment E: The oxidation catalyst of any of Embodiment A to Embodiment D, wherein the oxygen activation metal comprises cobalt (Co) or manganese (Mn).

Embodiment F: The oxidation catalyst of any of Embodiment A to Embodiment E, wherein the active phase comprises cobalt (III) oxide ($Co_2O_3$), manganese (IV) oxide ($MnO_2$), manganese (III) oxide ($Mn_2O_3$), or a mixture thereof.

Embodiment G: The oxidation catalyst of any of Embodiment A to Embodiment F, wherein the support is a macroporous support comprising pores having an average pore size of greater than or equal to about 50, 60, 70, 75, 80, 90, or 100 microns (μ).

Embodiment H: The oxidation catalyst of any of Embodiment A to Embodiment G, having a liquid pore volume, as measured by gravimetric liquid absorption, that is greater than or equal to about 0.1, 0.2, or 0.3 mL/g, or in the range of from about 0.2 to about 0.24 mL/g.

Embodiment I: The oxidation catalyst of any of Embodiment A to Embodiment H, wherein the support is spherical, cylindrical, tabular, or a combination thereof.

Embodiment J: The oxidation catalyst of any of Embodiment A to Embodiment I, wherein an average diameter or average largest dimension of the support is in a range of from about 1 to about 6, from about 2 to about 5, from about 2 to about 6, or less than or equal to about 7.5, 6, 5, or 4.5 mm, and/or greater than or equal to about 1, 1.5, or 2 mm.

Embodiment K: The oxidation catalyst of any of Embodiment A to Embodiment J, wherein the support comprises from about from about 0.1 to about 30, from about 1 to about 25, from about 5 to about 15 weight percent (wt %), less than or equal to about 30, 25, 20, or 15 wt %, and/or greater than or equal to about 5, 6, or 7 wt % silica.

Embodiment L: A method of producing an oxidation catalyst, the method comprising: forming an aqueous solution of an active metal precursor, wherein the active metal comprises cobalt (Co), manganese (Mn), iron (Fe), molybdenum (Mo), or a combination thereof; impregnating a support with the aqueous solution to form an impregnated support; and calcining to form the oxidation catalyst.

Embodiment M: The method of Embodiment L, wherein the active metal precursor comprises cobalt(III)nitrate hexahydrate, manganese(II)nitrate, iron(III)nitrate nonahydrate, ammonium heptamolybdate tetrahydrate, or a suitable decomposable metal complex, or a combination thereof.

Embodiment N: The method of Embodiment L or Embodiment M, wherein impregnating comprises incipient wetness impregnation.

Embodiment O: The method of any of Embodiment L to Embodiment N, wherein calcining comprises calcining in air.

Embodiment P: The method of any of Embodiment L to Embodiment O, wherein calcining comprises heating the impregnated support at a temperature of less than or equal to about 200° C., heating the impregnated support at a temperature of greater than or equal to about 200° C. and less than or equal to about 300° C., heating the impregnated support at a temperature of greater than or equal to about 300° C. and less than or equal to about 400° C., or a combination thereof.

Embodiment Q: The method of any of Embodiment L to Embodiment P further comprising: drying the impregnated support prior to calcining.

Embodiment R: The method of Embodiment Q, wherein drying comprises heating at a temperature in the range of from about 110 to about 250° C., from about 125 to about 200° C., from about 135 to about 175° C., or less than or equal to about 200° C.

Embodiment S: The method of any of Embodiment L to Embodiment R, wherein: the support comprises alumina or silica/alumina; the support has a Brunauer Emmett Teller (BET) surface area, as determined by ASTM D3663, that is less than or equal to about 20, 10, 5, or 1 $m^2/g$; the support is a macroporous support comprising pores having an average pore size of greater than or equal to about 50, 60, 70, 75, 80, 90, or 100 micrometers; and/or the support has a liquid pore volume, as measured by gravimetric water absorption, that is greater than or equal to about 0.1, 0.2, or 0.3 mL/g, or in the range of from about 0.2 to about 0.24 mL/g.

Embodiment T: A method of forming an oxidation product comprising benzaldehyde and acetophenone, the method comprising: contacting the catalyst of any of Embodiment A to Embodiment K with styrene and air in an oxidation reactor at a pressure of greater than or equal to atmospheric pressure and less than a pressure of 1, 3, or 5 atm.

Embodiment U: The method of Embodiment T, wherein the oxidation is performed at mild conditions including a temperature of less than or equal to about 140° C., 130° C., or 120° C.

Embodiment V: The method of Embodiment T or Embodiment U, wherein the oxidation reactor is a batch reactor or a continuous reactor.

Embodiment W: The method of Embodiment V, wherein the oxidation reactor is a continuous reactor, and wherein the method further comprises introducing air and a stream comprising the styrene into the oxidation reactor.

Embodiment X: The method of Embodiment W further comprising introducing the air via a distributor.

Embodiment Y: The method of Embodiment W or Embodiment X further comprising introducing the air and the stream comprising the styrene into the oxidation reactor concurrently.

Embodiment Z1: The method of any of Embodiment T to Embodiment Y, wherein the oxidation reactor is an upflow tubular reactor.

Embodiment Z2: The method of any of Embodiment W to Embodiment Z1, further comprising introducing the air at a gas hourly space velocity (GHSV) of greater than or equal to about 40, 30, or 20 $h^{-1}$, introducing the stream comprising styrene at a liquid hourly space velocity (LHSV) of less than or equal to about 0.4, 0.3, or 0.2 $h^{-1}$, or a combination thereof.

Embodiment Z3: The method of any of Embodiment W to Embodiment Z2 further comprising introducing the air at a gas hourly space velocity (GHSV) and introducing the stream comprising styrene at a liquid hourly space velocity (LHSV) such that a ratio of the gas hourly space velocity to the liquid hourly space velocity (GHSV/LHSV) is greater than or equal to about 60, 70, 80, 90, 100, 110, 120, 130, 140, 150, 160, or 170.

Embodiment Z4: The method of any of Embodiment T to Embodiment Z3, wherein the styrene is comprised in a tar stream from a styrene finishing column of a styrene production plant.

Embodiment Z5: The method of Embodiment Z4, wherein the tar stream is a bottoms product of a first styrene finishing column of a styrene separation section of the styrene production plant.

Embodiment Z6: The method of Embodiment Z5, wherein the tar stream comprises from about 85 to about 100, from about 88 to about 98, from about 90 to about 96, or greater than or equal to about 80, 85, 90, 95, 98 weight percent (wt %) styrene.

Embodiment Z7: The method of Embodiment Z6, wherein the tar stream further comprises one or more polymerization inhibitors, polymers, or a combination thereof.

Embodiment Z8: A method of reducing the fouling in a process for the production of styrene, the method comprising: producing, via oxidation of a crude styrene stream, a tar stream comprising styrene, or a combination thereof, an oxidation product comprising benzaldehyde, acetophenone, or a combination thereof, wherein the oxidation is effected with the oxidation catalyst of any of Embodiment A to Embodiment K; and introducing an additive stream comprising at least a portion of the oxidation product into a stream comprising styrene and byproduct divinyl benzene (DVB), whereby divinyl benzene (DVB) crosslinking is inhibited.

Embodiment Z9: The method of Embodiment Z8, wherein the tar stream comprising styrene is a slip stream of a bottoms stream from a styrene finishing column configured to separate the bottoms stream from an ethylbenzene (EB) recycle column into a bottoms stream comprising the tar stream and an overhead stream comprising styrene.

Embodiment Z10: The method of Embodiment Z9, wherein the slip stream comprises less than or equal to about 1, 5, 10, 15, or 20 weight percent (wt %) of the bottoms stream from the styrene finishing column.

Embodiment Z11: The method of any of Embodiment Z8 to Z10, wherein the additive stream is introduced into the stream comprising styrene and DVB such that a concentration of benzaldehyde, a concentration of acetophenone, or a sum of the concentration of benzaldehyde and the concentration of acetophenone is greater than or equal to about 0.001, 0.01 or 0.1 weight percent of the stream.

Embodiment Z12: The method of any of Embodiment Z8 to Embodiment Z11, wherein the stream comprising styrene and DVB into which the additive stream is introduced is a feed, recycle, or reflux stream to a distillation column downstream of an EB dehydrogenation reactor.

Embodiment Z13: The method of Embodiment Z12, wherein the distillation column comprises an EB recycle distillation column configured for the separation of a tops product comprising EB from a bottoms product comprising styrene, a distillation column configured for the separation of a tops product comprising benzene and toluene from a bottoms product comprising EB and styrene, or a styrene finishing distillation column configured for the separation of a tops product comprising styrene from a bottoms product comprising tar and styrene.

Embodiment Z14: The method of any of Embodiment Z8 to Embodiment Z13, wherein reducing the fouling comprises a reduction in the formation of insoluble polystyrene, soluble polystyrene, or both, of at least 1, 10, 50, or 100% relative to the same process absent the additive stream.

Embodiment Z15: The method of any of Embodiment Z8 to Embodiment Z14, wherein the additive stream further comprises a polymerization inhibitor having a boiling point of above 195° C., 200° C., 250° C., or 300° C.

Embodiment Z16: The method of Embodiment Z15, wherein the polymerization inhibitor is selected from dinitrophenols, TMPO compounds (e.g., 4-hydroxy-2,2,6,6-tetramethylpiperidine 1-oxyl), quinone derivatives, or a combination thereof.

Embodiment Z17: The method of any of Embodiment Z8 to Embodiment Z16, wherein the oxidation product is formed via the method of any of Embodiment T to Embodiment Z7.

Embodiment Z18: 21. The method of any of Embodiment Z8 to Embodiment Z17, wherein the oxidation is effected in the presence of an oxidation catalyst comprising: a porous support; and an active phase comprising an oxygen activation metal comprising cobalt (Co), manganese (Mn), iron (Fe), molybdenum (Mo), or a combination thereof Embodiment Z19: A system for the production of styrene via dehydrogenation of ethylbenzene (EB), the system comprising: one or more dehydrogenation reactors operable to contact EB and steam with a dehydrogenation catalyst under dehydrogenation conditions to yield a crude styrene effluent comprising styrene and byproduct divinyl benzene (DVB); a heat exchange apparatus configured to reduce the temperature of the crude styrene effluent to provide a cooled crude styrene effluent; a separations apparatus configured to separate an offgas and/or a condensate from the cooled crude styrene effluent and thus provide a dehydrogenation mixture; a distillation section operable to separate the dehydrogenation mixture into one or more streams comprising benzene, toluene, ethylbenzene, or a combination thereof, a tar stream comprising polymer, additives, species having a higher boiling point than that of styrene, and styrene, and a stream comprising styrene; an oxidation unit configured to produce, via oxidation of a portion of the tar stream, an oxidation product stream comprising oxidation products including benzaldehyde, acetophenone, or a combination thereof, wherein the oxidation unit comprises the oxidation catalyst of any of Embodiment A to Embodiment K; optionally a separator configured to separate the oxidation product stream into an additive component stream comprising a higher concentration of the benzaldehyde, the acetophenone, or the combination thereof than the oxidation product stream from an oxidation residue stream; and one or more recycle lines whereby at least a portion of the oxidation product stream, at least a portion of the additive component stream, or both can be combined with the crude styrene effluent, the cooled crude styrene effluent, the dehydrogenation mixture, a feed, recycle, or reflux to a distillation column of the distillation section, or a combination thereof.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference, to the extent that they provide exemplary, procedural or other details supplementary to those set forth herein.

What is claimed:

1. A method of reducing the fouling in a process for the production of styrene, the method comprising:
producing, via oxidation of a crude styrene stream, a tar stream comprising styrene, or a combination thereof, an oxidation product comprising benzaldehyde, acetophenone, or a combination thereof; and
introducing an additive stream comprising at least a portion of the oxidation product into a stream comprising styrene and byproduct divinyl benzene (DVB), whereby divinyl benzene (DVB) crosslinking is inhibited.

2. The method of claim 1, wherein the tar stream comprising styrene is a slip stream of a bottoms stream from a styrene finishing column configured to separate the bottoms stream from an ethylbenzene (EB) recycle column into a bottoms stream comprising the tar stream and an overhead stream comprising styrene.

3. The method of claim 1, wherein the stream comprising styrene and DVB into which the additive stream is introduced is a feed, recycle, or reflux stream to a distillation column downstream of an EB dehydrogenation reactor.

4. The method of claim 3, wherein the distillation column comprises an EB recycle distillation column configured for the separation of a tops product comprising EB from a bottoms product comprising styrene, a distillation column configured for the separation of a tops product comprising benzene and toluene from a bottoms product comprising EB and styrene, or a styrene finishing distillation column configured for the separation of a tops product comprising styrene from a bottoms product comprising tar and styrene.

5. A method of forming an oxidation product comprising benzaldehyde and acetophenone, the method comprising:
contacting an oxidation catalyst with styrene and air in an oxidation reactor at a pressure of greater than or equal to atmospheric pressure and less than a pressure of 5 atm, the oxidation catalyst comprising:
a porous support; and
an active phase comprising an oxygen activation metal comprising cobalt (Co), manganese (Mn), iron (Fe), molybdenum (Mo), or a combination thereof.

6. The method of claim 5, wherein the oxidation is performed at mild conditions including a temperature of less than or equal to about 140° C.

7. The method of claim 5, wherein the oxidation reactor is a continuous reactor, and wherein the method further comprises introducing air and a stream comprising the styrene into the oxidation reactor.

8. The method of claim 7:
further comprising introducing the air at a gas hourly space velocity (GHSV) of greater than or equal to about 40 $h^{-1}$, introducing the stream comprising styrene at a liquid hourly space velocity (LHSV) of less than or equal to about 0.4 $h^{-1}$, or a combination thereof; and/or
further comprising introducing the air at a gas hourly space velocity (GHSV) and introducing the stream comprising styrene at a liquid hourly space velocity (LHSV) such that a ratio of the gas hourly space velocity to the liquid hourly space velocity (GHSV/LHSV) is greater than or equal to about 60.

9. The method of claim 5, wherein the styrene is comprised in a tar stream from a styrene finishing column of a styrene production plant.

10. The method of claim 9:
wherein the tar stream is a bottoms product of a first styrene finishing column of a styrene separation section of the styrene production plant; and/or
wherein the tar stream comprises greater than or equal to about 80 weight percent (wt %) styrene.

11. The method of claim 5, wherein the oxidation catalyst further comprises from about 0.2 to about 4 weight percent (wt %) of the active phase as appropriate oxide phase and on the total weight of the oxidation catalyst after calcining.

12. The method of claim 5, wherein the porous support of the oxidation catalyst is a low surface area support having a Brunauer Emmett and Teller (BET) surface area, determined by ASTM D3663, that is less than or equal to 20 $m^2/g$.

13. The method of claim 5, wherein the oxygen activation metal of the oxidation catalyst comprises cobalt (Co) or manganese (Mn).

14. The method of claim 13, wherein the active phase of the oxidation catalyst comprises cobalt (III) oxide ($Co_2O_3$), manganese (IV) oxide ($MnO_2$), manganese (III) oxide ($Mn_2O_3$), or a mixture thereof.

* * * * *